United States Patent
Cooper et al.

(10) Patent No.: US 7,842,264 B2
(45) Date of Patent: Nov. 30, 2010

(54) PROCESS AND APPARATUS FOR CARBON CAPTURE AND ELIMINATION OF MULTI-POLLUTANTS IN FLUE GAS FROM HYDROCARBON FUEL SOURCES AND RECOVERY OF MULTIPLE BY-PRODUCTS

(75) Inventors: Hal B. H. Cooper, Kirkland, WA (US); Robert E. Tang, Dallas, TX (US); Donald E. Degling, Rye Brook, NY (US); Thomas K. Ewan, Dangerfield, TX (US); Sam M. Ewan, Dallas, TX (US)

(73) Assignee: Cefco, LLC, Dallas, TX (US)

( * ) Notice: Subject to any disclaimer, the term of this patent is extended or adjusted under 35 U.S.C. 154(b) by 367 days.

(21) Appl. No.: 12/080,317

(22) Filed: Apr. 2, 2008

(65) Prior Publication Data

US 2008/0250715 A1    Oct. 16, 2008

Related U.S. Application Data

(60) Provisional application No. 60/923,373, filed on Apr. 12, 2007.

(51) Int. Cl.
| | |
|---|---|
| B01D 53/34 | (2006.01) |
| B01D 53/50 | (2006.01) |
| B01D 53/56 | (2006.01) |
| B01D 53/62 | (2006.01) |
| B01D 53/64 | (2006.01) |
| B01D 53/74 | (2006.01) |

(52) U.S. Cl. .................... 423/210; 423/220; 423/215.5; 423/242.1; 423/235; 423/246; 423/245.1; 422/168; 422/169; 422/170; 422/176; 435/161; 435/166; 518/700; 585/500; 568/840; 570/246; 44/300; 526/59

(58) Field of Classification Search ................. 423/210, 423/220, 215.5, 242.1, 235, 246, 245.1; 422/168, 422/169, 170, 176; 435/161, 166; 518/700; 585/500; 568/840; 570/246; 44/300; 526/59
See application file for complete search history.

(56) References Cited

U.S. PATENT DOCUMENTS

| 467,264 | A | 1/1892 | Raymond |
| 723,531 | A | 3/1903 | Jackson |
| 925,711 | A | 6/1909 | Lilley |

(Continued)

OTHER PUBLICATIONS

European Patent Office, International Search Report, Aug. 21, 2008.

Primary Examiner—Timothy C Vanoy
(74) Attorney, Agent, or Firm—Jackson Walker L.L.P.

(57) ABSTRACT

A multiple stage apparatus and process using aerodynamic reactors and aero-coalescers in sequence for the selective capture and removal of purified carbon dioxide gas, the sequential capture and removal of mercury, metal and particulate aerosols by a recycling chemical generation-regeneration system using alkali metal chloride solution following multiple oxidations of mercury vapor, and nitric oxide in sequence, selective capture and removal of sulfur dioxide and nitrogen dioxide by two stage absorption by a recycling chemical generation-regeneration system using alkali metal hydroxide-carbonate-bicarbonate solution together with sequential oxidation to alkali metal sulfate and alkali metal nitrate compounds through evaporation and crystallization. Carbon dioxide capture and recovery is achieved in sequence by selective thermal decarbonation from an alkaline liquid followed by recovery as a purified gas stream.

36 Claims, 13 Drawing Sheets

U.S. PATENT DOCUMENTS

| | | | |
|---|---|---|---|
| 3,812,656 A | 5/1974 | Barnhart |
| 3,852,408 A | 12/1974 | Ewan et al. |
| 3,852,409 A | 12/1974 | Martin et al. |
| 3,894,851 A | 7/1975 | Gorman |
| 3,898,308 A | 8/1975 | Baum |
| 3,912,469 A | 10/1975 | Ewan et al. |
| 4,141,701 A | 2/1979 | Ewan et al. |
| 4,272,499 A | 6/1981 | Cason et al. |
| 4,369,167 A | 1/1983 | Weir, Jr. |
| 4,425,313 A | 1/1984 | Cooper |
| 4,426,364 A | 1/1984 | Cooper |
| 4,921,886 A | 5/1990 | Ewan et al. |
| 6,132,692 A | 10/2000 | Alix et al. |
| 6,315,976 B1 | 11/2001 | Phinney |
| 6,334,990 B1 | 1/2002 | Phinney |
| 6,375,824 B1 | 4/2002 | Phinney |
| 6,447,574 B1 | 9/2002 | Frier, Jr. et al. |
| 6,638,342 B2 | 10/2003 | Gansley et al. |
| 6,676,912 B1 | 1/2004 | Cooper et al. |
| 6,969,486 B1 | 11/2005 | Cooper et al. |
| 7,052,662 B2 | 5/2006 | Duncan et al. |
| 2003/0143140 A1 | 7/2003 | Hwang |
| 2006/0185985 A1 | 8/2006 | Jones |
| 2010/0137634 A1* | 6/2010 | Ding et al. .......... 560/347 |

* cited by examiner

SECTION A-A

FIGURE 7: ULTRAVIOLET PHOTOLYSIS

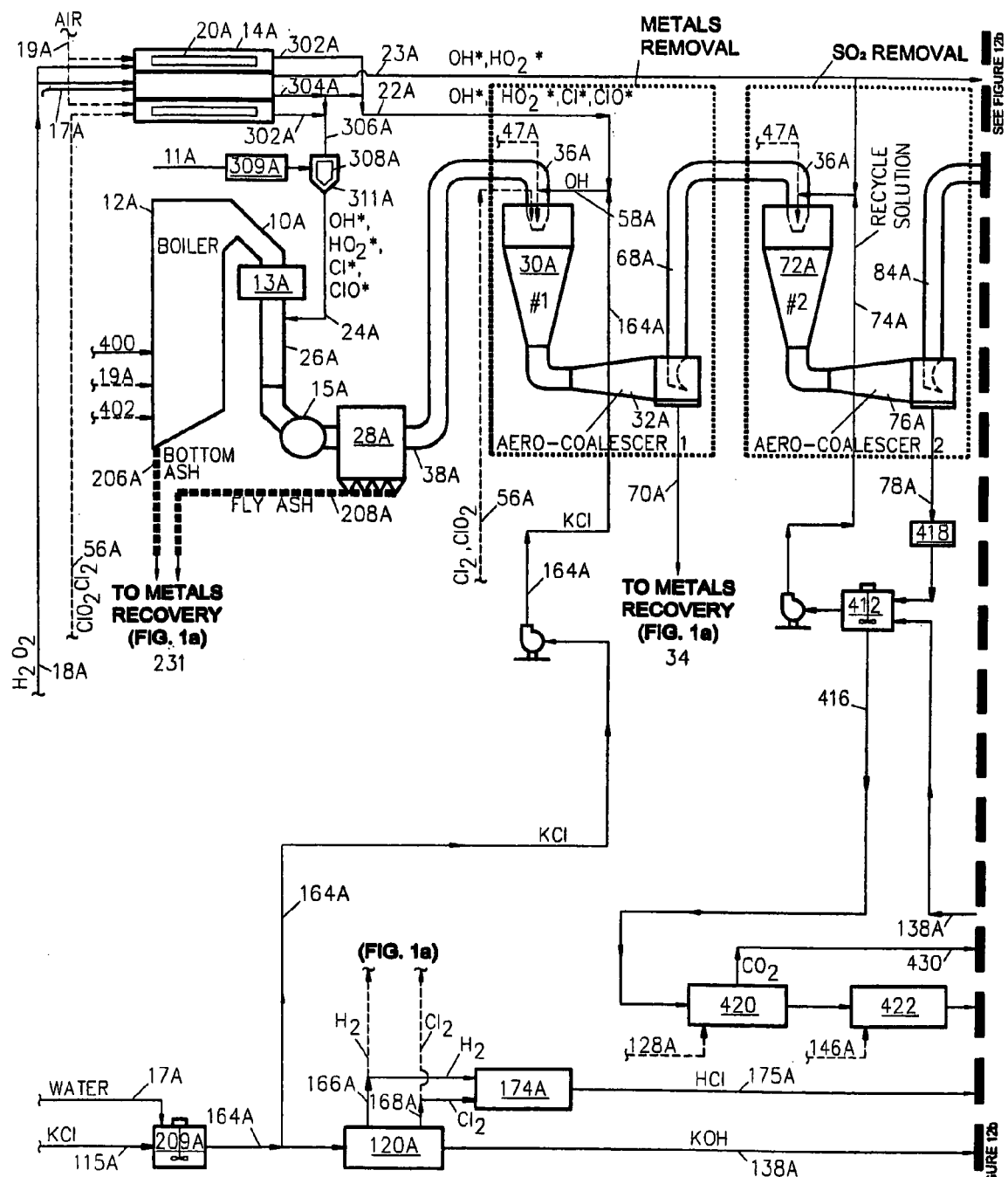
FIGURE 12a - PROCESS FOR MAXIMIZING CO2 RECOVERY & PRODUCTION

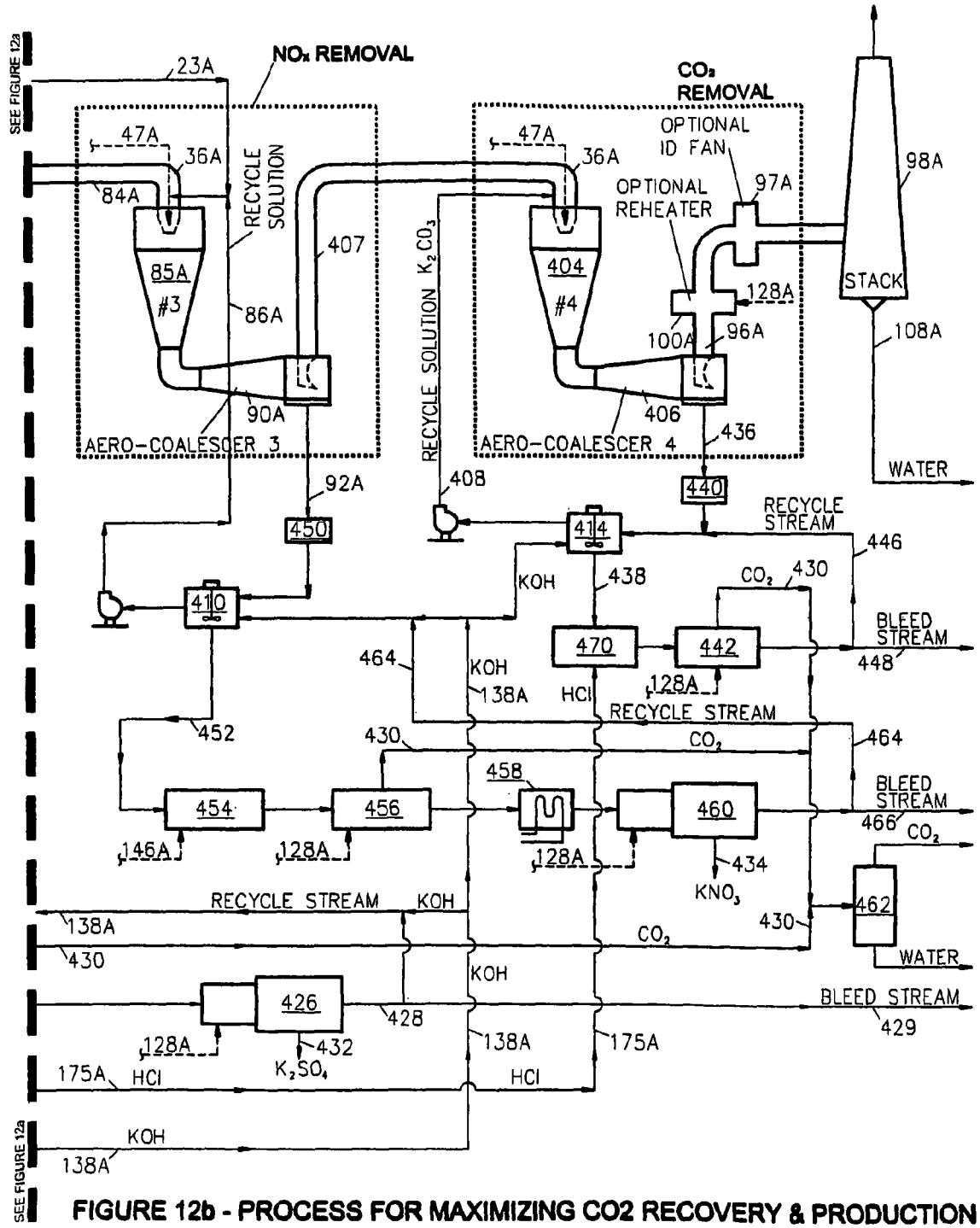
FIGURE 12b - PROCESS FOR MAXIMIZING CO2 RECOVERY & PRODUCTION

PROCESS AND APPARATUS FOR CARBON CAPTURE AND ELIMINATION OF MULTI-POLLUTANTS IN FLUE GAS FROM HYDROCARBON FUEL SOURCES AND RECOVERY OF MULTIPLE BY-PRODUCTS

This application claims priority to U.S. Provisional Patent Application Ser. No. 60/923,373, entitled "Process and Apparatus for Carbon Capture and the Elimination of Multi-pollutants in Flue Gas From Fossil-Fuel Fired Sources and the Recovery of Multiple by Products Therefrom" filed on Apr. 12, 2007, the entire content of which is hereby incorporated by reference.

BACKGROUND

This invention relates to processes for selective capture and removal of purified carbon dioxide gas, the selective removal and recovery of sulfur dioxide and nitrogen oxides plus heavy and trace metals, such as, but not limited to mercury, selenium, cadmium, arsenic, germanium, uranium and beryllium from gaseous mixtures containing these constituents, and especially from flue gas streams having low concentrations. These gaseous mixtures include combustion flue gas or off-gases produced from the burning of coal, oil, natural gas and other hydrocarbon fuels in power plants and industrial, agricultural and municipal furnaces and from similar emission sources.

It is particularly difficult to remove, by conventional means, the lower valence nitrogen oxides such as nitric oxide and trace metals including mercury vapor from these flue gas mixtures without prior preoxidation steps at the low concentrations at which they occur. It is also difficult to remove, by conventional means, the sulfur dioxide and carbon dioxide from these flue gas streams because of liquid solubility concerns in spite of their somewhat greater concentrations occurring separately or in the presence of other materials.

All of the above constituents are considered as air pollutants with a variety of adverse effects in the atmosphere and associated human environment. Sulfur dioxide and nitrogen oxides are air pollutants found at moderate concentrations in flue gas streams with well-established and regulated emission standards and ambient air quality standards by many countries. Mercury vapor and similar trace metallic constituents are air pollutants which are present at very low concentrations in flue gas streams which are potential problems with regard to human health, for which emission standards are only beginning to be developed. Carbon dioxide is a gaseous constituent found at higher concentrations in these flue gas streams, which is being increasingly linked as a contributor to the currently attributed global warming and climate change.

The present invention permits compliance with these regulatory mandates for air pollution control in a manner, which permits their recovery as commercially viable by-products in quantity and quality such that controlling and reusing these constituents may become profitable in the best case, and in the worst case as less costly than the conventional means of emissions control.

The present invention includes an aerodynamic reactor system, in which the heavy metal and particulate aerosols are removed and in which sulfur dioxide, carbon dioxide and nitrogen oxides are separated from the effluent gas stream following oxidation of mercury vapor, nitrogen oxides and organic compounds.

Various forms of wet scrubbers have been disclosed previously. For example: Raymond U.S. Pat. No. 467,264 shows an early method of purifying smoke by moistening it with steam and then separating the solid particles centrifugally. Jackson U.S. Pat. No. 723,531 discloses an apparatus for condensing smoke, fumes or gases by the use of a pair of water sprays and separating the particles by gravity or by filtration. British Pat. No. 925,711 discloses a liquid dust filter in which the dust-containing gas is accelerated through a narrowing passage or nozzle and then directed against a liquid stream. Gorman U.S. Pat. No. 3,894,851 utilizes water droplets condensed from steam to mix with a polluted gas. Thereafter, the wetted particulate is separated in a cyclone separator. Barnhart U.S. Pat. No. 3,812,656 discloses a fan driven venturi through which the dirt-laden air is drawn. Water is sprayed into the throat of the venturi to wet the dirt-laden air, and the dirt and water are separated by gravity while the air is exhausted through the fan. Another form of venturi scrubber is disclosed in Baum U.S. Pat. No. 3,898,308 which provides a series of adjustable water jets at the throat of the venturi for gas/liquid contact.

More recently, a series of patents have issued in which fine particulate is captured by encapsulating or entraining the particulate in small droplets and thereafter causing the droplets to grow in size until they can readily be separated from the gas in accordance with centrifugal or flow detachment separation principles. These patents include Ewan, et al. U.S. Pat. No. 3,852,408; Martin, Ewan et al. U.S. Pat. No. 3,852,409; Ewan, et al. U.S. Pat. No. 3,912,469; Ewan, et al. U.S. Pat. No. 4,141,701; Cason, Ewan et al. U.S. Pat. No. 4,272,499, and Frier, Bass and Ewan U.S. Pat. No. 6,447,574 B1. In the latter patent the flue gas flowing through the system is entirely subsonic and the system is not capable of separately removing the particulate pollutants and the acid gas pollutants, or to reclaim them separately and regenerate them as valuable by-products. Moreover, none of the above patents contains any technology or mechanism concerning the capture of carbon dioxide. Certain of the above patents also disclose the removal of acidic gases such as sulfur dioxide and nitrogen oxides by means of alkaline chemical reagents such as sodium carbonate, sodium hydroxide, calcium oxide, calcium hydroxide, magnesium oxide, ammonium hydroxide and potassium permanganate. The end products of these removal processes for all of the above patents are either relatively low value materials such as gypsum or ammonium based fertilizers or disposable material such as sludge or solid waste residues.

Another aspect of the present invention is the separation and recovery of sulfur, nitrogen, and carbon compounds from the effluent gases in a form such as potassium sulfate or potassium nitrate which are valuable as fertilizers. Carbon dioxide which is captured and recovered may be sold as an end product, to be used for the enhanced tertiary recovery of oil, or for enhanced vegetable crop growth, or to produce algae for BioDiesel fuel, or to be sequestered. Carbon dioxide may also be utilized as a feedstock to produce commercial end-products such as methanol, ethanol (which may be considered as a feedstock for making BioFuels and transportation fuels) and ethylene (with ethylene, or more specifically ethylene dichloride, being an intermediate for polyvinyl chloride plastics production).

A process for the removal and recovery of nitrogen and sulfur oxides from gaseous mixtures such as combustion gases from power plants is disclosed in Cooper U.S. Pat. Nos. 4,425,313 and 4,426,364. In these patents the nitrogen and sulfur oxides are removed separately or together and are converted to sulfates and nitrates which may be useful as fertilizers. However, these earlier patents do not disclose how to separate gases so as to prevent the heavy metals and very fine particulate matter (PM) in the flue gas: (1) from contaminating the recovered sulfates and nitrates to make them marketable as fertilizers in a purer form, or (2) from aerodynamically or chemically escaping capture and being released to the atmosphere. As noted above, heavy metals such as mercury and other trace metals and very fine particulate matter normally escape capture and are now recognized as air pollutants which can significantly affect the environment and human health.

The Powerspan Electro-Catalytic Oxidation Process described in U.S. Pat. Nos. 6,132,692 and 7,052,662 is an ammonium rather than potassium based process (utilizing both dry and wet removal processes), which produces, as its end products, the less valuable ammonium based fertilizers such as the potentially dangerous and explosive mixtures of ammonium nitrates and ammonium sulfates. Also, the Powerspan process employs catalytic oxidation of elemental mercury and nitric oxide which is less effective than the high temperature gas phase thermal oxidation employed in the present invention, and Powerspan will result in possible catalyst plugging or fouling.

The Airborne Sodium Bicarbonate Process described in U.S. Pat. Nos. 6,315,976; 6,375,824 and 6,334,990 is a sodium based conventional chemistry process in contrast to the present invention which is normally in its preferred embodiment a potassium based combined aerodynamics physics and chemistry process. As a result, the Airborne Process cannot recover carbon dioxide and requires the additional use of ammonium hydroxide as a make-up chemical, which results in the formation of ammonium sulfate and the potentially hazardous ammonium nitrate situation similar to the aforementioned Powerspan process.

Gansley U.S. Pat. No. 6,638,342 recently discloses another ammonium based conventional chemistry process for the removal of sulfur dioxide, nitrogen dioxide and trace or toxic metals. As the trace metals are removed simultaneously with the sulfur dioxide and the nitrogen dioxide, the ammonium based fertilizer (produced by the Gansley process), is inherently contaminated by the precipitated metallic salts, without offering any remedy for the aforesaid toxicity problem raised. The Gansley process merely attempts to partially remove the toxic metals; however, such effort appears to be very costly in energy consumption and inefficient, and could not produce commercially marketable and non-toxic by-products from the flue gas.

The Skyonic Sodium Carbonate Process described in the U.S. Patent Publication No. 20060185985 employs the electrolysis of sodium chloride to sodium hydroxide in order to capture carbon dioxide as sodium carbonate and bicarbonate. The carbon dioxide gas (which is intended to be a purified gas) is then liberated from the carbonate solution by hydrochloric acid produced from the hydrogen and chlorine. However, the process does not involve the removal of sulfur oxides, nitrogen oxides and trace metals, and produce only the low value sodium carbonate and bicarbonate as by-product chemicals. Since Skyonic makes no provision to oxidize the mercury or other trace metals upstream of its bubbling process, then the metallic solids would be accumulating in the liquid solution. In addition, the unreacted and untreated elemental mercury vapor can either escape aerodynamically in the body of the flue gas stream, or can also accumulate in the absorbing liquid and then be released together with the carbon dioxide gas to contaminate it. The Skyonic Process claims to be only able to remove 70 percent of the carbon dioxide emitted while consuming 30 percent of the power plant's overall energy output. Therefore, there are considerations of toxicity, impracticality and cost inefficiencies.

Cooper U.S. Pat. Nos. 6,969,486 and 6,676,912 relate to the photolytic oxidation of hydrogen peroxide to hydroxyl free radicals using ultra-violet light to oxidize nitric oxide, carbon monoxide and organic vapors respectively to nitrogen dioxide, carbon dioxide and water. These earlier patents do not state that elemental mercury vapor can be oxidized to mercuric salts separately and selectively upstream, and therefore to become separated from the nitrogen oxides scrubbing step downstream, thereby avoiding contamination of the potassium nitrates (similarly for the other trace metals). The solution is herein addressed, disclosed and produced by the present invention which solves the problem. Furthermore, in all of the afore-mentioned earlier patents, there is also no provision to recover and produce methanol or ethanol or ethylene, in contrast to the present invention.

SUMMARY

Selective oxidation of elemental mercury, and addition of chlorine dioxide, chlorine gas, and chloro, chloroxyl and hydroxyl free radicals produced from hydrogen peroxide for downstream removal of mercury particulates and metal aerosols by alkali metal chloride reaction through aerodynamic reactor systems. Recovery of mercuric and other metallic compounds solids by alkali metal sulfate salt recycling to regenerate alkali metal hydroxide and/or chloride materials for electrolysis cells. Chlorine and hydrogen gas production from alkali metal chloride electrolysis to generate alkali hydroxide alkaline liquid for absorption of sulfur dioxide, nitrogen dioxide and carbon dioxide in sequences by the aerodynamic reactors and aero-coalescers. Chlorine reaction with ethylene produced from ethanol fermentation with hydrogen catalysis to produce ethylene dichloride intermediate with additional ethylene reaction to produce vinyl chloride monomer and polyvinyl chloride plastic. Hydrogen reaction with chlorine to produce hydrochloric acid for mercury and other metals, such as for aluminum extraction and recovery to regenerate alkali metal chloride and/or hydroxide electrolysis feed, and for product recycling and recovery. Hydrogen and carbon dioxide reaction to become synthesis gas for producing ethanol, methanol, ethylene and the derivatives thereof from the collected carbon dioxide captured from the flue gas streams.

The present invention makes it possible to capture and remove effectively (1) the large concentration of carbon dioxide from the flue gas streams generated from coal-fired power plants and other hydrocarbon fuel industrial sources; (2) the moderate concentration of sulfur dioxide and nitrogen oxides from these flue gas streams; and (3) the small concentration of mercury vapor and other metallic and other fine particulate aerosols from these gas streams. These air pollutants so removed may then be recovered from the flue gas streams after treatment and absorption through the multiple consecutive phases of preoxidation, removal, recovery and regeneration for each category of materials in both the gaseous and particulate forms through a multiple series of cyclic processes. The air pollutants may be converted to the collectible from the uncollectible forms, and then removed from the power plant or industrial burner flue gas streams. The expected subsequent conversion and recovery of these pollutants to usable by-products, together with the regeneration of the collecting liquid mediums as recycling absorbing solutions through a series of cyclic processes, show a great conservation of consumable resources and a highly economical process for sulfur oxides and nitrogen oxides recovery to produce potassium sulfate and potassium nitrate fertilizers, and carbon dioxide recovery so that carbon dioxide can be converted to a variety of usable chemical and clean fuel by-products.

This invention relates to the selective capture and removal of purified carbon dioxide gas, the selective processes for removal and recovery of sulfur dioxide and nitrogen oxides and other gases from gas stream mixtures plus mercury and other metallic aerosol emissions at coal-fired power plants and other hydrocarbon fuel industrial sources. These air pollutants are matters of increasing concern with regard to protection of public health and the environment, which require a comprehensive recycling generative and regenerative system for emission control employing alkali chlorides as recycled feed materials for removal and recovery, on an effective and economic basis, to produce usable chemical and fertilizer by-products. These flue gas streams are initially treated by a multiple stage aerodynamic reactor employing preoxidation of nitric oxide to nitrogen dioxide, and mercury vapor to ionic mercury compounds, plus carbon monoxide and organic compounds to carbon dioxide and water vapor. The gaseous process involves treatment with a choice of compressible fluid, such as steam/air (or a gas), together with water, chlorine, chlorine dioxide, hydrogen peroxide and a choice of photolyzed chlorine, chlorine dioxide and hydrogen peroxide in sequence, in an aerodynamic reactor system with an alkali metal chloride reagent solution, followed by removal of the mercury salts and metallic aerosols and particulates in a first stage aero-coalescer gas/liquid separation unit.

The resulting chemical removal and recovery systems then remove mercury compounds and other metallic aerosol salts from the first stage aero-coalescer effluent liquid system by means of filtration, precipitation and demineralization in series followed by acidic and alkaline extractions. The resulting recovered solids are then treated with hydrochloric acid and alkali metal hydroxide for metals recovery from the solid residuals streams. The regenerated alkali metal halide solution is returned to the aerodynamic reactor as a recycled liquid stream from the solids separation steps to create a recycling regenerative process in order to minimize additional chemical makeup requirements.

The continuing-forward moving flue gas stream following metals and particulates removal is then passed through a second aerodynamic reactor system (which preferably includes an aero-coalescer for the gas/liquid separation function although other gas/liquid separators may be used) using recycled reagent solution of alkali metal hydroxide, carbonate and bicarbonate to remove sulfur dioxide and carbon dioxide. Then the continuing balance of the gas stream travels to a third stage aerodynamic reactor system (which preferably also includes an aero-coalescer for the gas/liquid separation function) using the parallel recycled reagent solution of alkali metal hydroxide, carbonate and bicarbonate to remove nitrogen dioxide and the remaining carbon dioxide.

Both the second stage aerodynamic reactor as well as the third stage aerodynamic reactor(s) use their own respective aero-coalescers to separate the gas stream from the liquid effluent stream. The liquid effluent streams from the second stage sulfur dioxide removal system, and the third stage nitrogen dioxide removal system, are then treated sequentially by means of oxidation, decarbonation and evaporation plus crystallization to facilitate removal of the respective alkali metal sulfate and nitrate salts as recovered solids. The carbon dioxide is captured and recovered as a separate purified gas stream from the exhausts of the decarbonation units by the decomposition of alkali metal bicarbonates to carbonate salts in both the sulfur dioxide and nitrogen dioxide removal steps. The recovered alkali metal carbonate solutions generated from the evaporation and crystallization steps in both the sulfur dioxide and nitrogen dioxide removal steps are then diluted with water and recirculated and returned to their respective reactors after addition of makeup alkali metal hydroxide from the chemical generation-regeneration system. As a result, additional removal of the pollutants in the on-coming flue gas stream can then take place by using the recycled and regenerated liquid reagent solution.

The separate recycling chemical generation-regeneration system employs parallel alkali metal chloride and ethylene processing units using existing technologies. The ethylene is produced from the catalytic thermal conversion of ethanol by reaction with hydrogen from the separate electrolysis units, with the ethanol produced by upstream fermentation reaction of corn or other agricultural sources or bio-sources, or by synthesis from hydrogen and carbon dioxide. The alkali metal chloride salt solution is passed through an electrolysis cell where alkali metal hydroxide is produced as a liquid solution for addition as makeup chemical for the sulfur dioxide and nitrogen dioxide absorption steps. There are also hydrogen and chlorine gas streams produced at the opposite electrodes where the hydrogen gas goes to the separate catalytic reactor for conversion of methanol or ethanol into ethylene and all their related derivatives, or for the separate chemical by-product production of hydrogen peroxide for subsequent use in the preoxidation step for the boiler flue gas. In addition, both methanol and ethanol and all their related derivatives, including such as BioFuels can be synthesized from the hydrogen generated from the electrolysis step and the carbon dioxide removed from the flue gas stream as usable and valuable by-products. All of the by-product production as described above are the result of this invention.

The present invention, for the first time, provides the unexpected complete solution to the problem of removing all pollutants, contaminants, and greenhouse gases from a combustion gas mixture so that the final effluent gas is essentially pure air. Almost forty years ago, the aerodynamic process evidenced, primarily, by the various Ewan patents issued beginning in the 1970's, demonstrated the ability to remove even submicronic particulate, metals, and acid gases from a combustion gas as a slurry. At best, however, the slurry comprised a product such as gypsum contaminated by the particulate and metals and little, if any, carbon dioxide could be captured. On the other hand, the Cooper process which had also been developed beginning almost forty years ago and exemplified by the Cooper patents issued in the 1970's relied on standard chemical reactors which, although able to separate sulfur and nitrogen products, but these products were necessarily contaminated by the particulates and metals. Despite the fact that the Ewan and Cooper processes were available to those skilled in the art for at least thirty years, no one, until the present inventors, conceived a particular way to combine these processes, that were each individually deficient, to form a process, that for the first time, was capable of removing all the pollutants and contaminants separately so as to provide uncontaminated and valuable by-products and, at the same time, eliminate the problem of greenhouse gases. A tremendous amount of effort and money have been spent on clean coal technology, coal gasification, and flue gas treatment but none of this effort has yielded an economical process capable of removing over 90% of the carbon dioxide along with sulfur dioxide and oxides of nitrogen. In fact, several proposed processes have been found to be uneconomical and development programs were cancelled. In view of these failures and deficiencies of some of the inventors own work, the success of the present invention is both unobvious and unexpected.

BRIEF DESCRIPTION OF THE DRAWINGS

FIGS. 12a and 12b show a flow-chart of a variation of the system of FIGS. 1a and 1b particularly adapted for maximizing the recovery and production of carbon dioxide.

The identification numbers for the Figures are also listed in Appendix 1.

DETAILED DESCRIPTION OF THE PREFERRED EMBODIMENTS

This invention makes it possible to capture and remove effectively: (1) the large concentration of carbon dioxide from the flue gas streams generated from coal-fired power plants and other hydrocarbon fuel industrial sources; (2) the moderate concentration of sulfur dioxide and nitrogen oxides from these flue gas streams; and (3) the small concentration of mercury vapor and other metallic and fine particulate aerosols from these gas streams. These air pollutants so removed may then be recovered from the flue gas streams after treatment and absorption through the multiple consecutive phases of preoxidation, removal, recovery, and regeneration for each category of materials in both the gaseous and particulate forms through a multiple series of cyclic processes. The air pollutants may be converted to the collectible from the uncollectible forms, and then removed from the power plant or industrial burner flue gas streams. The expected subsequent conversion and recovery of these pollutants to usable by-products, together with the regeneration of the collecting liquid mediums as recycling absorbing solutions through a series of cyclic processes, show a great conservation of consumable resources and a highly economical process for sulfur oxides and nitrogen oxides recovery to produce potassium sulfate and potassium nitrate fertilizers, and carbon dioxide recovery so that carbon dioxide can be converted to a variety of usable chemical and fuel by-products.

The preoxidation pretreatment process takes place in order to convert the nitric oxide, elemental mercury vapor, and other trace metals vapors with characteristics behaving like mercury vapor, plus carbon monoxide and organic vapors, plus fine particulate aerosols from their uncollectible states to collectible forms. The nitric oxide is converted to nitrogen dioxide and the elemental mercury to ionic mercury salt compounds and as larger size particles more amenable to capture and removal from the flue gas stream. The preoxidation process for pretreatment of the nitric oxide to nitrogen dioxide takes place through a series of gas phase oxidation reactions employing photolyzed hydrogen peroxide plus chlorine and chlorine dioxide gas in an alkali metal chloride liquid reagent solution. In addition, the preoxidation step results in the partial oxidation of carbon monoxide to carbon dioxide as well as of the organic vapors to carbon dioxide and water vapor so that they can be removed more easily from the gas stream.

Figure 1A:
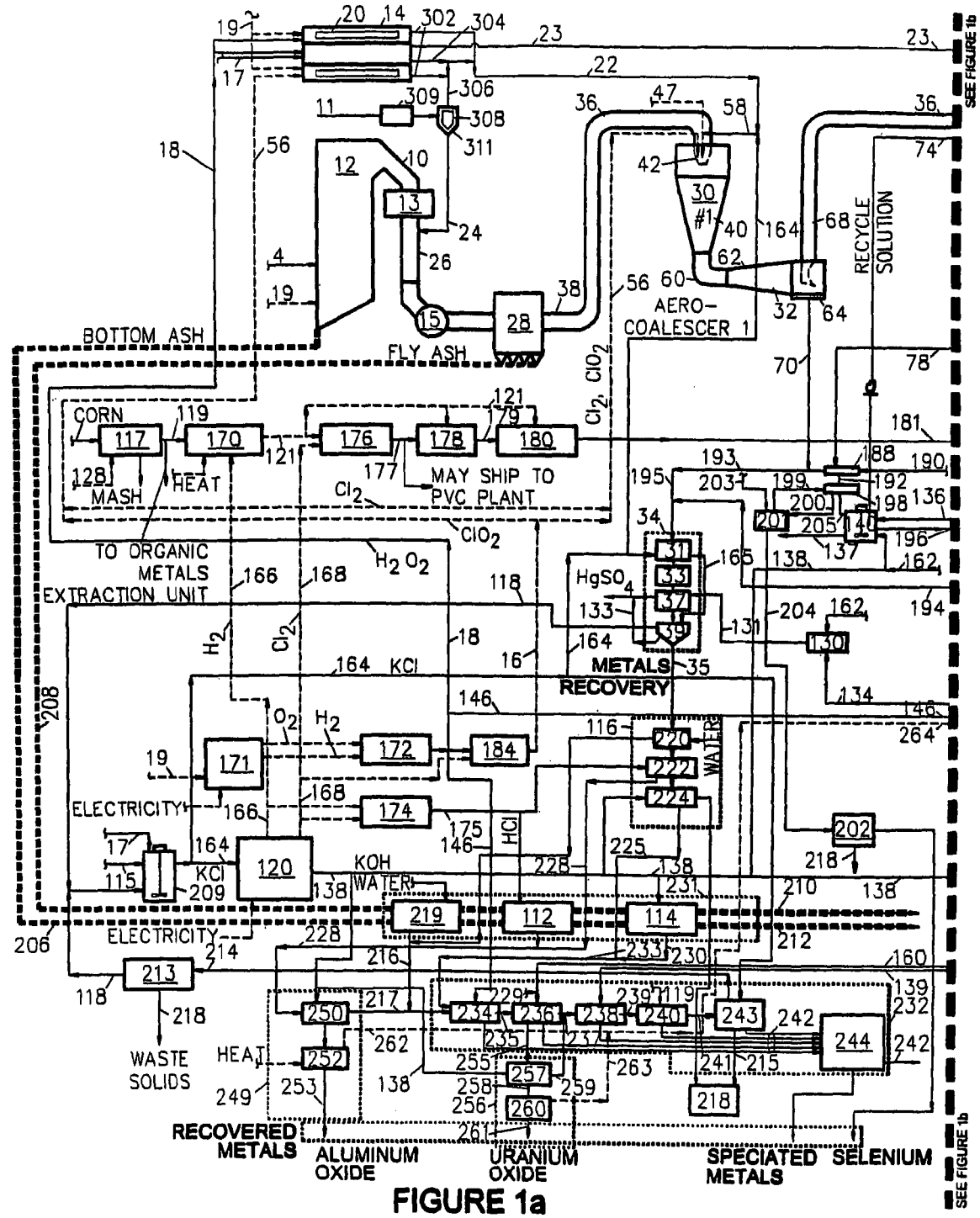
FIGS. 1a and 1b show a flow chart of the system by which particulates, heavy metals, sulfur dioxide, nitrogen oxides and carbon dioxide are removed and recovered from the effluent gas of a hydrocarbon fuel combustion process, and their respective recycling chemical reagent generation-regeneration systems for by-product recovery.
Figure 7:
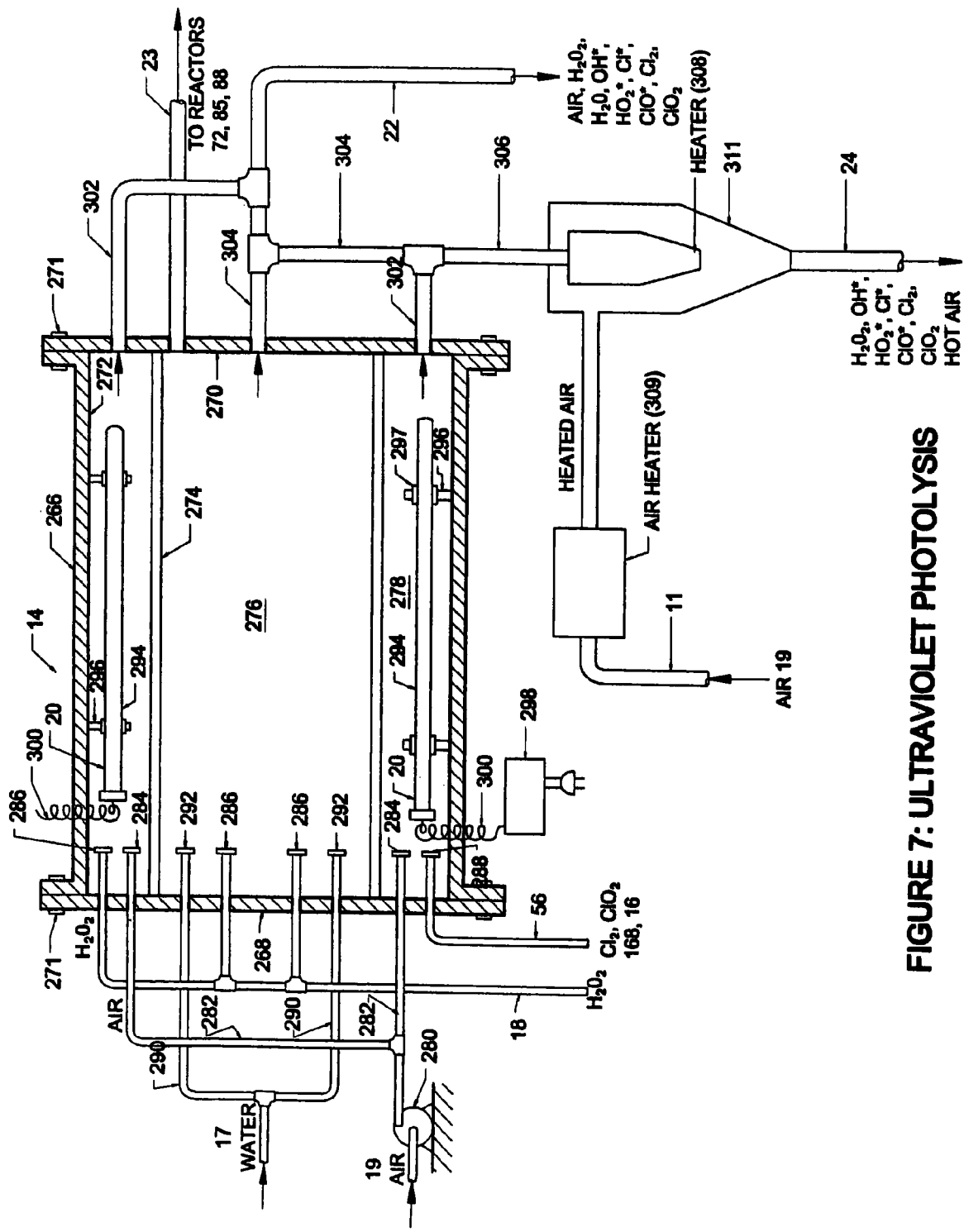
FIG. 7 shows the ultraviolet photolysis unit for producing free radicals from liquids and gases.

Referring now to FIGS. 1a and 7, the preoxidation pretreatment process for conversion of the insoluble elemental mercury vapor to the soluble oxidized mercury salt compounds occurs through a described gas phase multiple-step treatment. Streams of chlorine and chlorine dioxide 56 and hydrogen peroxide 18 are fed into the photolysis unit 14 and are subjected to ultraviolet light 20 so as to produce a stream of chloro, chloroxyl, hydroxyl and hydro-peroxyl free radicals 22, 306. In FIG. 7, a portion of the stream of free radicals in line 306 is directed through a heater for free radicals 308 to vaporize the liquid components of the stream. Preferably, air 19 passing through feed duct 11 is heated by an air heater 309 and introduced into mixing chamber 311 where it mixes with the vaporized stream of free radicals, water, water vapor and hydrogen peroxide. The combined stream leaves the mixing chamber 311 via the duct 24 and is injected into the boiler exit duct 26 where the temperature of the flue gas is still high. Preferably, as shown on FIG. 1a, that point may be between the air preheater 13 and the economizer 15. In some plants, the economizer may be located upstream of the air preheater. In this event, the injection point preferably is upstream of the economizer to take advantage of the higher flue gas temperature which facilitates the desired oxidation reactions to occur so that the pollutants are then converted to more readily collectible forms.

The exit duct 26 from the boiler communicates with the entrance of the primary particle collection device 28 which may, for example, be an existing electrostatic precipitator, cyclone separator or bag house. The function of the primary collection device is to separate the large particulate matter, such as fly ash, from the hot flue gas and, if necessary, to reduce the temperature of the hot gas 10 to the range of 140° to 160° C. (285° to 320° F.) and to provide humidification of the gas stream. In lieu of the primary collection device 28, in some plants a conditioning chamber comprising a spray tower fitted with water sprays may be used. The pretreatment process for converting the fine particulate aerosols from the uncollectible to the collectible form involves passage of the flue gas through the first stage aerodynamic reactor 30 which involves both sonic and supersonic free jets in the presence of liquid solutions to create turbulent mixing, nucleation, particle growth and condensation to facilitate removal from the flue gas stream by the aero-coalescer 32 to separate the liquid from the gas phase. This step allows the captured particulate matter and oxidized mercury compounds to be removed in a liquid solution for subsequent passage to a metal separation and recovery unit 34, and where the liquid reagent solution is then reconstituted and recycled for economic reuse in the gas phase removal process for removing additional air pollutants.

Figure 2:
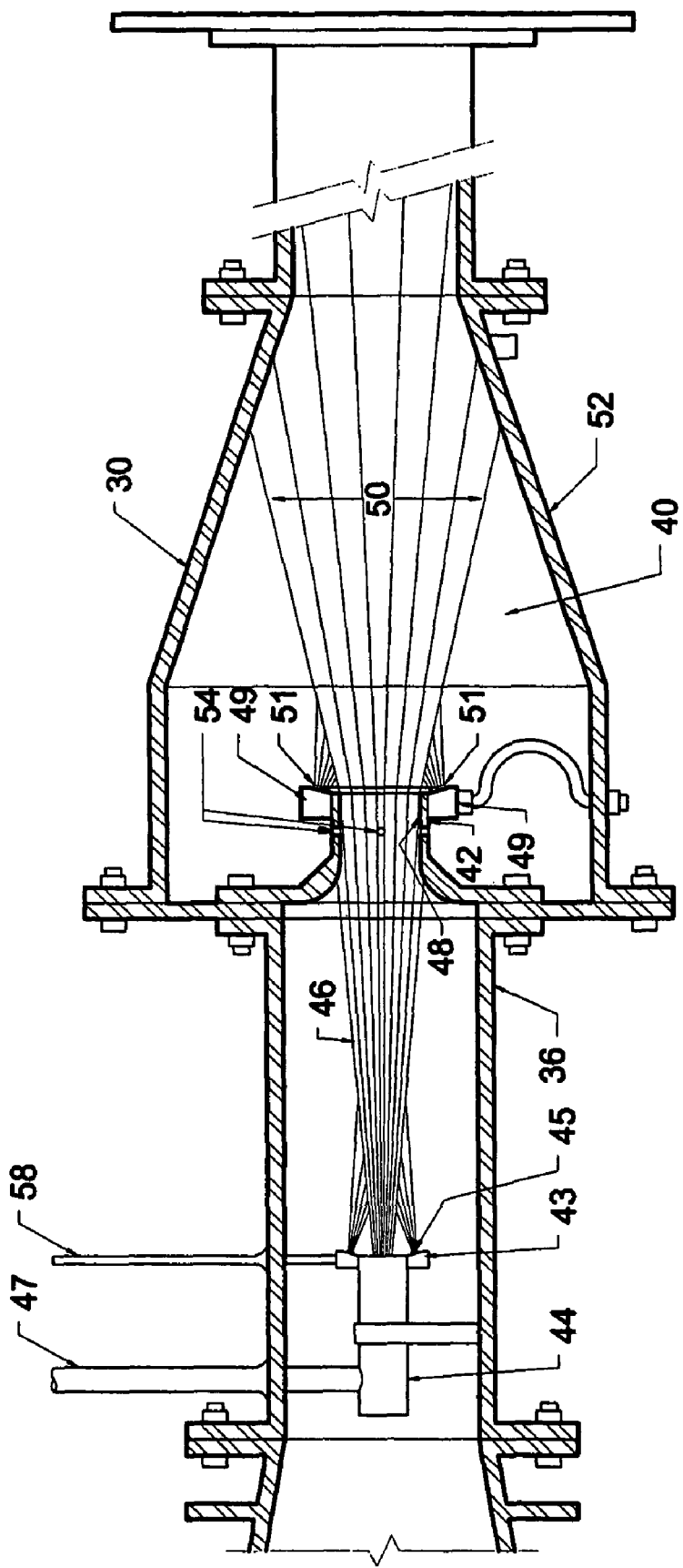
FIG. 2 shows, partly in section, the arrangement of the supersonic and subsonic nozzles and the related mixing/reaction chamber.
Figure 5:
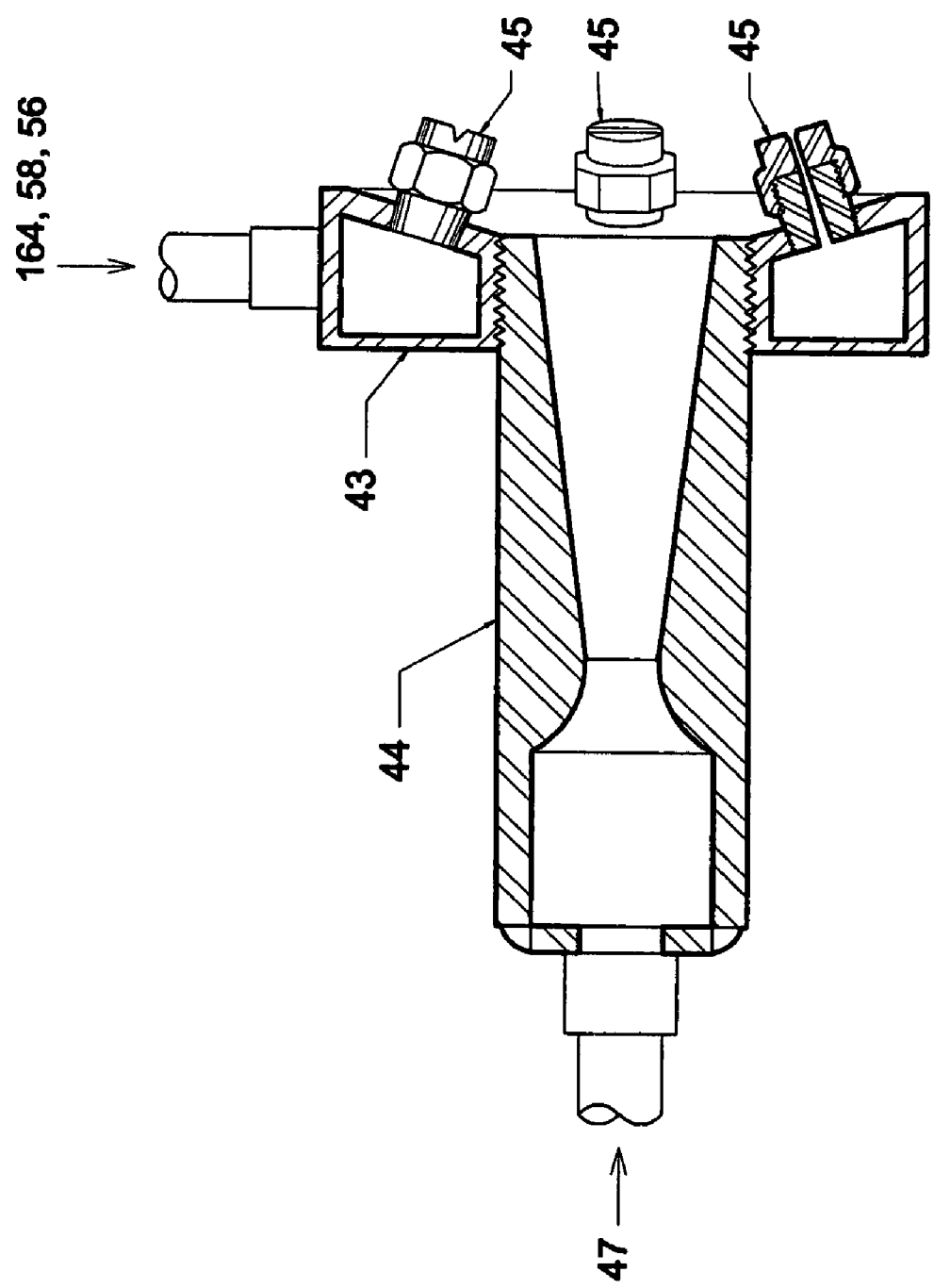
FIG. 5 shows the detailed cross-sectional view of the supersonic nozzle for steam or air injection.

Referring now to FIGS. 1a, 2 and 5, the first aerodynamic reactor 30 comprises an entry duct 36 which communicates between an exit duct 38 from the primary collection device 28 and a mixing/reaction chamber 40. A subsonic nozzle 42 is located between the exit of the entry duct 36 and the entrance of the mixing/reaction chamber 40. A nozzle which is preferably a supersonic nozzle 44 is located within the entry duct 36 and may be driven by a compressible fluid such as steam 47 or air or a gas. By "supersonic" this invention means that the compressible fluid exits from the supersonic nozzle 44 at a speed greater than the speed of sound in the medium of the polluted gas stream in the flow of the ductwork 36 where the supersonic nozzle is located. A manifold 43, positioned near the exit end of the preferably supersonic nozzle 44, is fitted with multiple spray nozzles 45. Water and (if used) a solution of chemical reagents including an alkali metal chloride salt such as potassium or sodium chloride 164, via 58, and free radicals 22, may be introduced through the spray nozzles 45 as a liquid or as a vapor. If desired, chlorine and chlorine dioxide gases 56 may also by introduced through the nozzles 45 into the gas stream. The supersonic free jet 46 exiting from the supersonic nozzle 44 contacts the throat 48 of the subsonic nozzle 42 and functions as an ejector pump to draw, force and ram the polluted effluent gas 10 into and through the supersonic free jet 46 and thence through the subsonic nozzle 42 and into the subsonic free jet 50. In the science of aerodynamics, the term "free jet" means a jet blast which is unbounded, unconfined and unrestrained. In this invention, the use of the supersonic nozzle, which produces a supersonic free jet, is preferable to the use of a subsonic nozzle for the initial driving and mixing function because the supersonic nozzle provides greatly improved mixing performance with lower energy requirements than the subsonic nozzle. On the other hand, the subsonic nozzle 42 located at the entrance to the reaction chamber is adequate for the physical and chemical reactions occurring within the combined jet formed by means of the compressible fluid, the injected liquids, together with the polluted gas stream. If desired, additional water or a solution of chemical reagents may preferably be introduced into the subsonic free jet 50 by means of a manifold 49 fitted with spray nozzles 51 and located around the subsonic nozzle 42 at the exit end thereof. Due to the shock waves and energy extant in the supersonic free jet 46 and the molecular diffusion by Brownian movement in both the gaseous and liquid phases, intimate and unavoidable collision occurs between the polluted gas 10, the reagents (if used), and the supersonic free jet 46 so that there is effective and intimate gas/liquid contact and mixing of all the molecules in the gas stream.

The mixing/reaction chamber 40 includes a section of decreasing cross-section 52 which is contacted by the subsonic free jet 50 so as to form a second ejector pump. A series of aspirational openings herein called apertures 54 are situated in the throat 48 of the subsonic nozzle 42. The apertures 54 communicate with a zone of much larger interior diameter within the mixing/reaction chamber 40, but outside the subsonic free jet 50. As a result of the gas flowing through the throat 48 of the subsonic nozzle 42 with the aspirating or sucking inwardly effect of the apertures 54, the pressure in the region of the mixing/reaction chamber 40 outside the subsonic free jet 50 is reduced to sub-atmospheric pressure. The pressure immediately downstream from the subsonic nozzle 42 also becomes subatmospheric because of the increasing velocity of the nozzle exit jet and the expansion of space into which the gas is ejected and expanded. There occurs a noticeable and rapid cooling of the gas stream so affected. Since the effluent gas stream, having been thoroughly mixed with the liquid droplets or vapor, and (if used) the chemical reagents, passes and exits through the subsonic nozzle to form a second turbulent free jet, it aspirates and produces a subatmospheric pressure zone outside in the region of the subsonic free jet 50. Thus the exiting gas associated with the subsonic free jet expands within the mixing/reaction chamber and experiences a rapid temperature drop, which enhances condensation of moisture on the sub-micronic particulates and aerosols that act as nucleation sites for their encapsulation into water droplets. Due to the turbulent conditions within the sub-sonic free jet, the droplets containing the sub-micronic particulates and aerosols rapidly grow in size from multiple collisions, impactions and nucleations, as well as further condensation, until they reach a size that can be easily separated from the effluent gas stream. The gas/liquid separation device is preferably an aero-coalescer in which the pollutant-containing droplets are aerodynamically separated in a chamber of increasing cross-section which removes the liquid and its entrained aerosols and particulates in liquid droplet form from the rest of the gaseous stream.

The subatmospheric pressure zone within aerodynamic reactor 30 supplements and assists the mixing actions in the free jet by removing the boundary layers surrounding the aerosols thereby enhancing the intended chemical reactions (if any) and the formation and growth of liquid droplets, which have encapsulated the particulate matter and chemical reaction products (if any), thus enabling the ensuing separation and collection by the aero-coalescer or other gas/liquid separator. This is the result of an aerodynamic reactor system and process being applied in the context of molecular physics and surface chemistry, which is different from conventional chemistry. Moreover, the internal auto-cleaning and removal efficiency of an aerodynamic system is a function of the energy supplied to the aerodynamic reactor, and may be controlled by adjusting the amount of pressurized steam or chemical reagents supplied to the aerodynamic reactor.

Although a single supersonic/subsonic nozzle assembly and mixing/reaction chamber are generally adequate for the removal of heavy metals and aerosols comprising very small particulates, a second similar nozzle assembly and mixing/reaction chamber may be mounted between it and the ensuing aero-coalescer or other gas/liquid separator, if desired. In like manner in an alternative arrangement, the single supersonic nozzle, as in FIG. 2, may be replaced by a plurality of small supersonic nozzles, as in FIG. 3, all directed toward the throat 48 of the subsonic nozzle 42. If desired, a portion, or all, of the chemical reagents referred to above may be introduced through one or more of the supersonic nozzles in liquid or vapor form. However, such reagents are preferably introduced through the manifolds and spray nozzles associated with the respective supersonic nozzles. Preferably, the supersonic/subsonic nozzle assembly and mixing/reaction chamber are positioned vertically so that the supersonic and subsonic free jets are directed vertically downwardly so as to facilitate rapid mixing and contact between the liquid droplets and the gas stream constituents. On the other hand, a horizontal assembly may also be arranged, though it may increase the physical space requirement of the site as a result.

Figure 3:
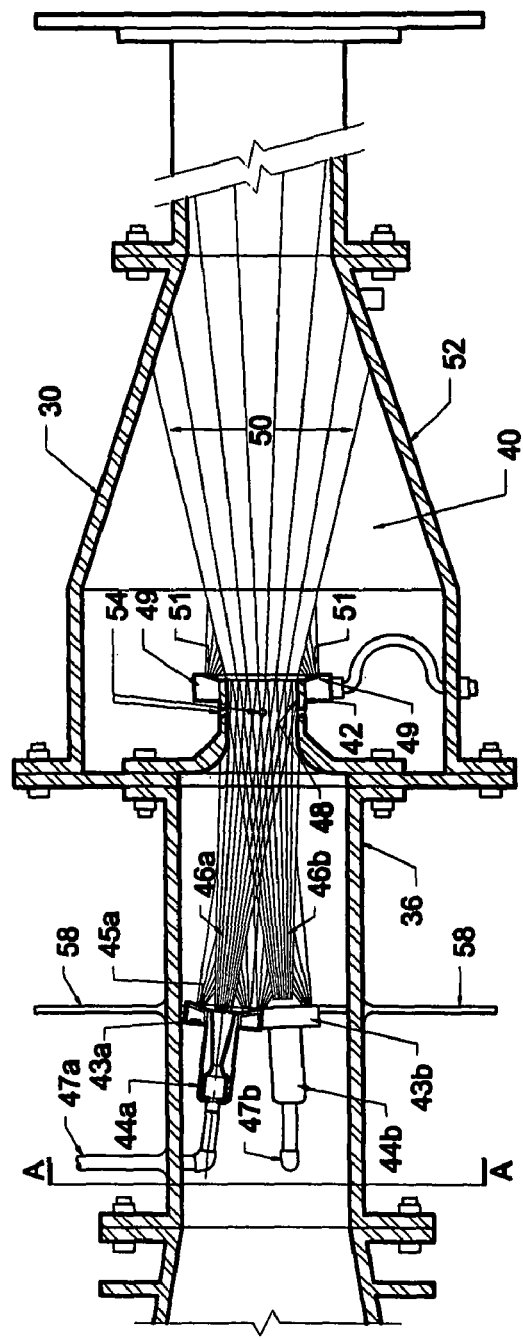
FIG. 3 shows, partly in section, an alternative nozzle arrangement employing a plurality of supersonic nozzles.
Figure 4:
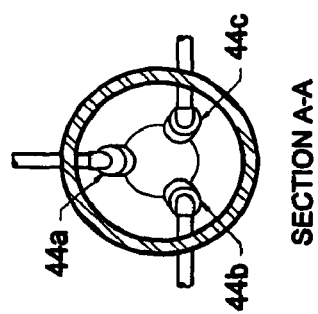
FIG. 4 shows a cross-section of the supersonic nozzle assembly taken along line A-A of FIG. 3.

FIGS. 3 and 4, respectively, show an alternative arrangement for the supersonic nozzle 44 of FIG. 2. In FIGS. 3 and 4, three supersonic nozzles 44a, 44b and 44c are shown. Each of the three nozzles 44a, 44b and 44c is directed toward the throat 48 of the subsonic nozzle 42. Steam 47 or air may be used to drive the supersonic nozzles 44a, 44b and 44c to facilitate effective gas/liquid contact. The free radicals hydroxyl and hydroperoxyl plus chloro and chloroxyl as well as the chemical reactants chlorine, chlorine dioxide and alkali metal chloride may be introduced through the manifolds 43a, 43*b* and 43*c* and through the spray or atomizing nozzles 45*a*, 45*b* and 45*c*. By an "atomizing nozzle", this invention means a nozzle capable of breaking a liquid into very small droplets when it injects the liquid. Although three supersonic nozzles are shown in FIGS. 3 and 4, it will be appreciated that additional nozzles may be provided, if desired. As shown on FIG. 1, (if used) the chemical reagents chlorine and chlorine dioxide enter the duct 36 via line 56 while alkali metal chloride and chloro, chloroxyl, hydroxyl and hydroperoxyl free radicals 22 enter the duct 36 via line 58. As noted above, these chemical reagents are preferably introduced into the supersonic jets 46 in liquid or vapor form, through the corresponding manifolds 43 and spray or atomizing nozzles 45, although they could be introduced into the gas stream 10 within the duct 36, and then mixed with the supersonic jet or jets 46.

Figure 6:
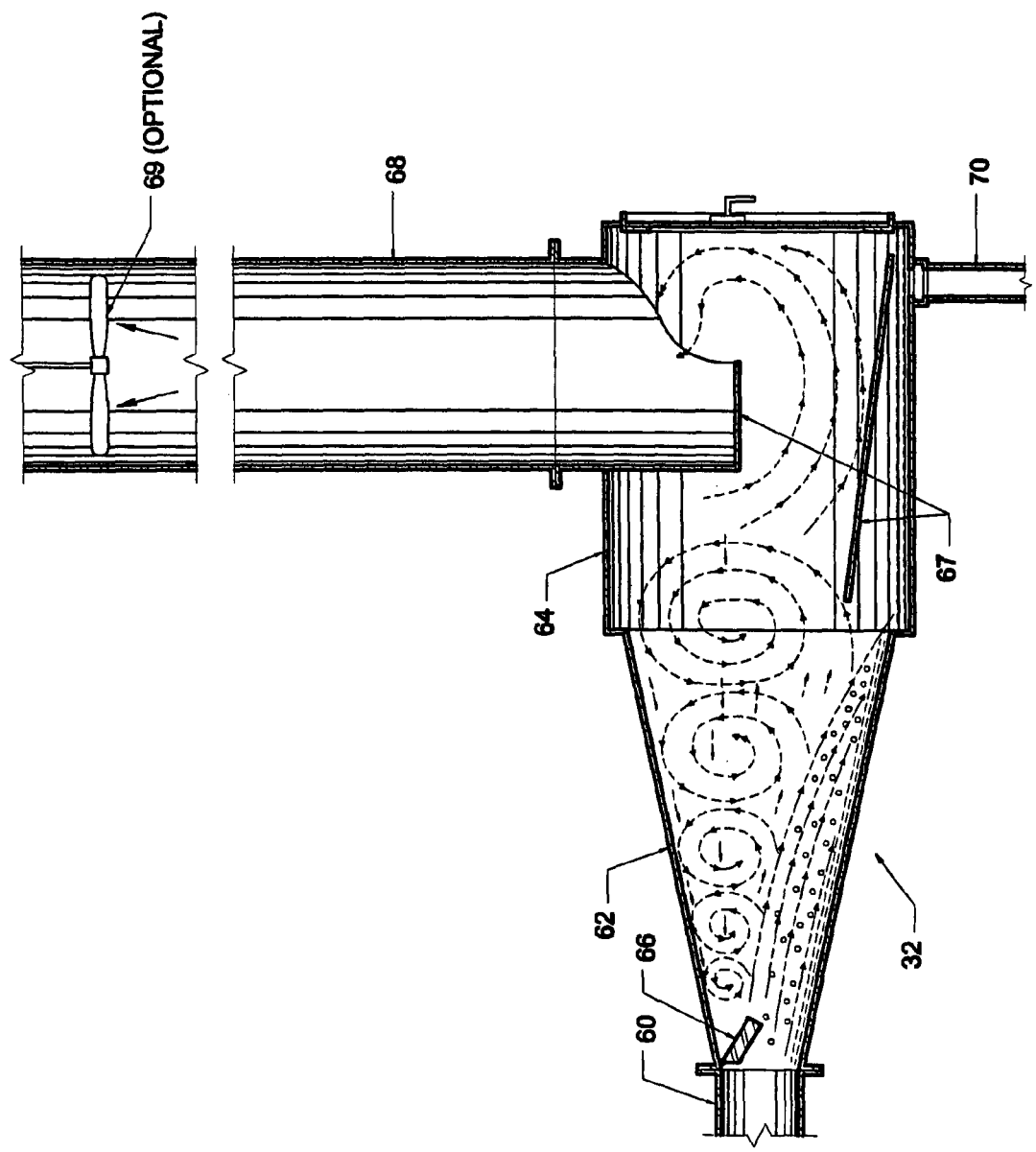
FIG. 6 shows the detailed cross-sectional view of the aero-coalescer for liquid separation from the flue gas stream.

The partially cleaned flue gas and the pollutant-containing droplets exit the vertically oriented aerodynamic reactor 30 into an elbow 60 and thence into the horizontally oriented aero-coalescer 32 as shown in FIG. 6. Referring to FIG. 6, the aero-coalescer 32 for liquid droplet separation from the gas comprises a portion of increasing cross-section 62 and a portion of constant or uniform cross-section 64. Aerodynamic flow separating means 66, which may be a fixed or adjustable or angled strip, barrier, blade or a fluid stream, is located near the entrance of the increasing cross-section portion 62 of the aero-coalescer 32. The flow separating means 66 causes the liquid droplet portion of the gas flow to be directed downwardly toward the wall of the aero-coalescer 32 while the gaseous portion of the gas flow in a spinning eddy effect lifts upward and leaves the aero-coalescer via the duct 68. The gaseous portion of the gas flow leaving the aero-coalescer 32 contains the sulfur dioxide, nitrogen oxides and carbon dioxide from the hot gas 10 while the separated liquid being heavier, and thus flowing downwardly, draining from the aero-coalescer via line 70 contains the particulate matter and heavy metals, trace metals and other particulates captured from the hot gas stream 10, which are then collected and recovered.

Although not wanting to be bound by any theory, discussions of possible mechanisms and theories are given below.

The Aerodynamic Mechanism

As appears from the above description of the first aerodynamic gas cleaning reactor (herein referred as ADGC), the ADGC apparatus itself is mechanically quite simple and includes no moving parts, and each of the three or four aerodynamic reactors (as used throughout the entire system and processes of this invention hereafter) are substantially identical, and so their respective descriptions are similar. However, the processes performed within each aerodynamic reactor and its respective aero-coalescer are quite sophisticated and unlike the processes performed in conventional pollution control equipment.

The supersonic nozzle 44 (or nozzles 44*a*, 44*b*, 44*c*) are located in the inlet duct 36 and, in conjunction with the subsonic nozzle 42, form an ejector pump which draws the polluted gas stream 10 through the system. The design of the supersonic and subsonic nozzles shown in FIGS. 2, 3 and 5 is well known to those skilled in the art and need not be described in detail here. Spray or atomizing nozzles 45 associated with the supersonic nozzles 44 spray the atomized water or chemical reagents directly into the supersonic free jet 46. The atomized liquid droplets are shattered and further reduced in size and intimately mixed with the supersonic free jet 46, which has been generated by nozzle 44 and moving at a speed in excess of 1,180 feet per second. For the free jet exiting the jet nozzle to form and to be fully effective, the cross-sectional area of the inlet duct 36 should be at least about four times greater than the cross-sectional area of the exit mouth of the jet nozzle 44. Smaller area ratios will adversely affect the performance of the reactor. Due, in part, to the shock waves and energy extant in the supersonic free jet 46, turbulent and intimate mixing of the polluted gas stream 10, which is traveling originally at a nominal speed of 40 to 60 feet per second, with the very fine droplets of water and chemical reagents (if used) occurs within the free jet 46 in the shock wave zone of the supersonic free jet 46. The mixture, after the turbulent mixing, blends their respective traveling speeds and averages to a speed of 150 to 250 feet per second.

As the gas stream mixture is pushed or forced into and passes through the subsonic nozzle 42, the velocity of this stream is greatly increased to sonic-range velocity at the exit mouth of nozzle 42 because the gaseous content is forced through nozzle 42. This accelerated stream now enters suddenly into a much larger-diameter reaction chamber 40, which has an interior chamber cross-sectional area at least four (4) to five (5) times greater than the cross-sectional area of the exit mouth of the subsonic nozzle 42, and the gas stream suddenly expands in volume, while the pressure of the stream suddenly drops to a subatmospheric level after entering into the chamber 40. As noted above, a smaller area ratio will adversely affect the performance of the reactor. Thus, in the subsonic free jet 50 as it issues from the subsonic nozzle 42, the pressure becomes noticeably subatmospheric and the temperature becomes noticeably cooler. Additionally, due to the aspirating or sucking inwardly effect of the apertures 54 in the throat 48 of the subsonic nozzle 42, the pressure in the mixing/reaction chamber 40 immediately outside the subsonic free jet 50 will also be subatmospheric for a certain distance. The lowered pressure results in a stripping of the surface boundary layer on the very small or atomized vapor or aerosol particles and droplets, and reagent (if used), whereby the aerosols, particles, droplets and the reagent (if used) are all brought into immediate contact with each other and react rapidly. Heat is absorbed in this process. Due to the very small size of the droplets and reagents (if used), the ratio of contact surface area-to-volume may be thousands of times greater than that associated with or involved in conventional chemical reactions under normal conditions. In addition, there is molecular diffusion or Brownian movement in both the gaseous and liquid phases of the turbulent gas/liquid mixture. If chemical reagents are used, the ions of the compounds react with their respective opposite-charged ions of their targets resulting in the intended reactions, and endothermic reactions take place where energy is absorbed.

As a result of the subatmospheric and endothermic conditions created within reaction chamber 40 using the principles of aerodynamic science, the intended chemical reactions may be completed in milliseconds, and the primary process or mechanism becomes one of molecular surface chemistry, not conventional chemistry. The intended reactions take place within a rapid temperature drop of up to about 150° F. The decreased temperature causes condensation of the water vapor on nucleation sites provided by the particulate and reaction products. Due to the turbulence within the subsonic free jet 50, the droplets encapsulating the particulates and the reaction products grow by extremely rapid and repetitive impaction, interception, diffusion, reaction, nucleation and condensation. Continuing impaction, interception, diffusion, reaction and nucleation are due, in part, to Brownian movement of the very small particles and ions. This process repeats itself in random order very rapidly and causes the "growth" of ever larger droplets and the encapsulation-re-encapsulation of ever more nucleating sites until the stream travels outside of and beyond the reaction zone.

As the mixture of gases and droplets travels towards the latter part of and beyond the reaction chamber 40, pressure recovery takes place: (1) exothermic conditions begin to take place which provide a temperature recovery of about 50° to 75° F., and (2) within the converging section 52, there begins a recovery of the pressure to a normal atmospheric level together with the continuing droplet growth. Thus, beyond the reaction zone, somewhere between the converging section 52 and the aero-coalescer 32, the intended chemical reactions reach a point of equilibrium, and the exothermic and positive pressure conditions of conventional chemistry are re-established.

The elbow 60 between the vertically oriented aerodynamic reactor 30 and the aero-coalescer 32 serves as an extended or additional mixing tube where further droplet growth by continuing impaction, nucleation and condensation occurs. As the gas mixture enters the aero-coalescer 32, it comprises a mixture of gases and relatively large droplets containing the captured heavy and trace metals and other particulates being encapsulated and re-encapsulated by condensation into very large droplets which can then be separated.

As shown in FIG. 6, the aero-coalescer 32 comprises a diverging section 62 which provides some additional pressure recovery for the gaseous phase constituents and a constant diameter section 64 with a flow separating means 66 located near the entry of the diverging section 62. The flow separating means 66 diverts the fully encapsulated liquid droplets toward the bottom wall of the aero-coalescer 32 and is designed to induce a series of spinning-eddies, which cause the remaining droplets to settle out in a liquid form while the gaseous phase constituents travel out and up through the stack exit duct 68. There may be one or more additional shaped flow separating means 67 located within the aero-coalescer designed to ensure the final separation of the more energized gas phase from the moisture-laden liquid droplets encapsulating the targeted reaction-product, which would be much less energized and cooler and would move downwardly, as liquid droplets, accumulating into streamlets, and passing out at the bottom of the catch-pan of the aero-coalescer. A fan 69 (if desired) may be located in the exit duct 68 to help pull the gaseous phase through and up the exit duct 68, and to make up for the combined pressure loss of 4 to 5 inches of water column, which occurs in the aerodynamic reactor 30 and may not be sufficiently recovered in aero-coalescer 32. While a separate fan 69 may be located in the exit duct from each coalescer, it may be more desirable to employ a single induced draft fan 97 at the end of the integrated multiple-staged aerodynamic reactor system and before the entry to the stack 98, or alternatively but less desirably, a forced draft fan before the entry to the first aerodynamic reactor, as the alternative engineering designs may require.

The partially cleaned gas which leaves the aero-coalescer 32 unit via duct 68 is directed into the inlet of a second aerodynamic reactor 72 for the removal of sulfur dioxide. A combined solution of alkali metal hydroxide plus carbonate and bicarbonate salts via line 74, plus the hydroxyl and hydroperoxyl free radicals via line 23 (if desired), is fed to the second aerodynamic reactor 72 through the respective spray or atomizing nozzles 45 associated with the supersonic nozzle 44 of that reactor. The reactor exit liquid and gas are separated in a second gas/liquid separator or aero-coalescer 76 with the exit liquid passing via line 78 to the sulfur dioxide and sulfur trioxide chemical recovery system to obtain chemical by-products. Sulfur dioxide removal is accomplished at efficiencies of 99.0 percent or greater by the aerodynamic process previously described. A portion of the carbon dioxide is also recovered along with the sulfur by-products in the liquid stream.

The partially cleaned gas (to a great extent containing $NO_x$ and the remaining $CO_2$) leaves the sulfur oxides reactor system 72, 76 via duct 84 and is directed into the entry of a third aerodynamic reactor 85 for nitrogen oxide removal. This reactor is substantially identical to the first and second aerodynamic reactors. It is fed by a second alkali metal hydroxide-carbonate-bicarbonate solution through line 86, and hydroxyl and hydroperoxyl free radicals through line 23 (if desired). The reagent solution is fed into the third aerodynamic reactor 85 through the respective spray or atomizing nozzles 45 associated with the supersonic nozzle 44 of that reactor. Since the chemical reactions with the nitrogen oxides proceed more slowly than those with the sulfur oxides, it may be desirable to provide a fourth aerodynamic reactor 88 in the same manner in series behind the third aerodynamic reactor 85. Recycle reagent solution 86 may also be introduced through the respective spray or atomizing nozzles 45 associated with the supersonic nozzle 44 of the fourth aerodynamic reactor 88 into the gas stream.

The gas and liquid droplets exiting the fourth aerodynamic reactor 88 are directed into the gas/liquid separator or aero-coalescer 90, where the spent reagent liquid 92 containing the alkali metal nitrite and nitrate components plus the remaining portion of the carbon dioxide, and the alkali metal carbonate-bicarbonate reagent solution are passed to the by-product recovery system similar to that used for sulfur dioxide. In the nitrogen oxides removal process, efficiencies of 99.0 percent or greater can be achieved by the aerodynamic process so described.

Figure 1B:
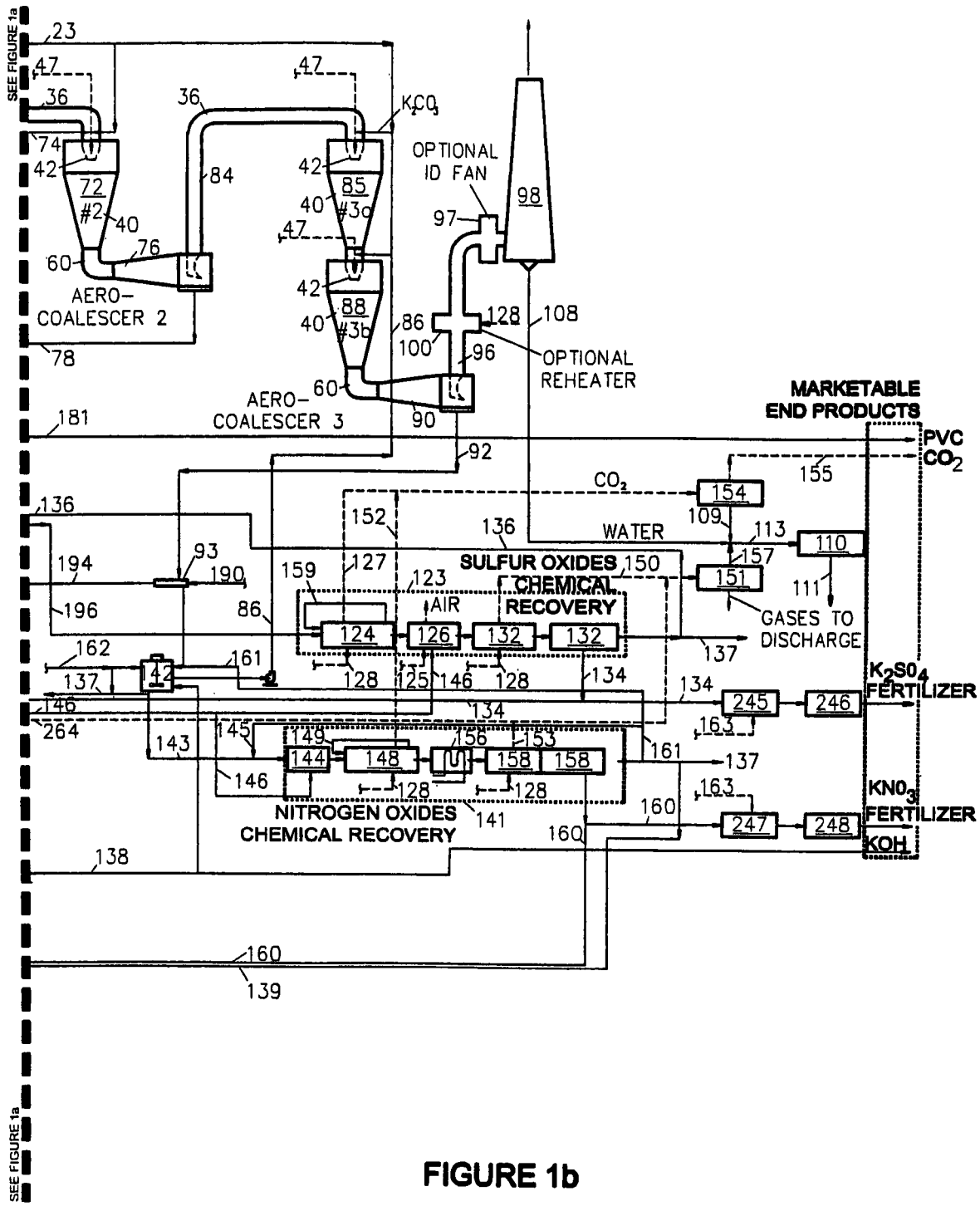

The cleaned gas from the nitrogen oxides aerodynamic reactors 85, 88 exits the system via duct 96. As explained earlier, it may be desirable to employ an induced draft fan 97 to assist the upward movement of the cleaned gas at this point. Prior to release to the stack 98 the cleaned gas may be reheated in reheater 100. In addition, it may be desirable to add a heater in one or more of the exit ducts 68, 84, 96 (as shown in FIGS. 1*a* and 1*b*) and 407 (as shown in FIG. 12*b*) to control the temperature of the gas stream entering the respective aerodynamic reactors 72, 85 (as shown in FIG. 1*b*) and 404 (as shown in FIG. 12*b*). Water recovered from the stack condensate liquid is conducted through line 108 to a water treatment plant 110 for subsequent reuse.

Comprehensive Recovery and By-Product Reclamation System

Figure 8:
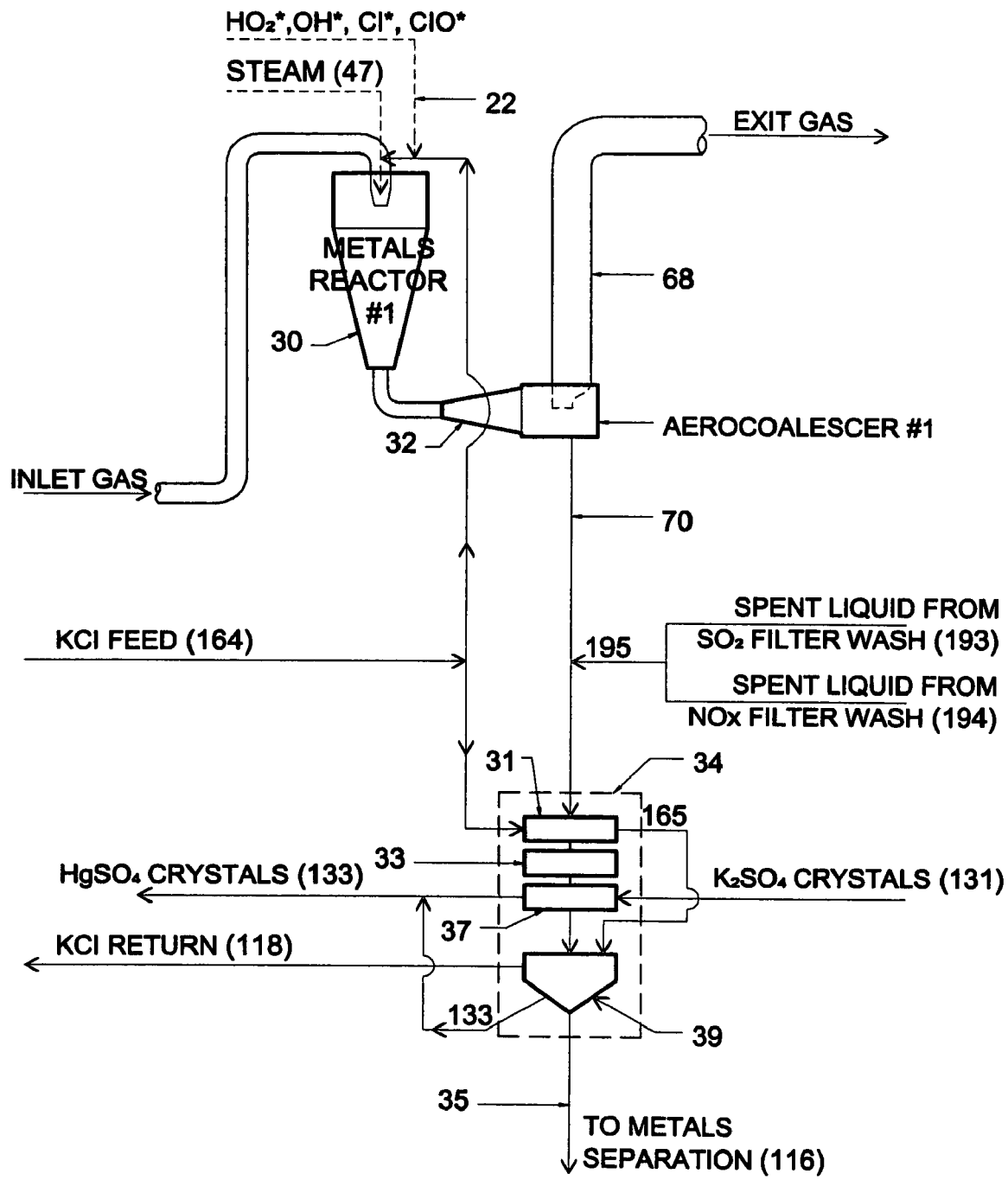
FIG. 8 shows the liquid treatment system for the removal and recovery of mercury from the flue gas.
Figure 9:
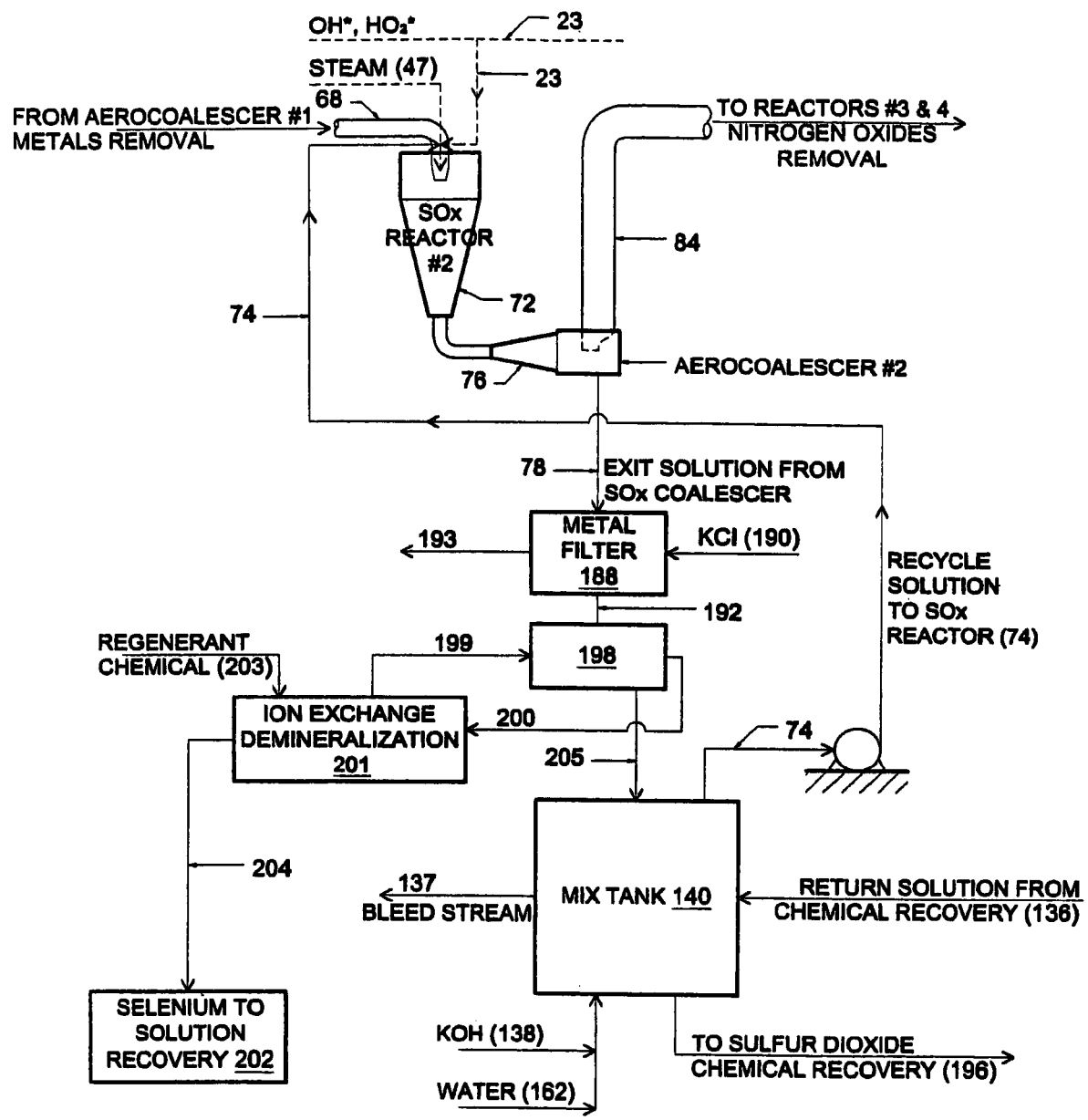
FIG. 9 shows the liquid treatment system for the removal and recovery of selenium from the flue gas.

Referring now to FIG. 9, the exit liquid 78 from the second aerodynamic reactor 72 and second aero-coalescer 76 for sulfur oxides removal first passes through a prefilter 188 for the removal of insoluble materials by washing with water or alkali metal chloride solution 190. The removed insoluble materials and the wash solution containing water and potash then go to the metals separation and recovery unit 34 (see FIG. 8), via line 193. The filtered spent reagent liquid 192 then passes to the selenium removal step before going to the recycle mix tank 140, via line 205. In the mix tank 140, the alkali metal carbonate return solution 136 from the evaporator-crystallizer 132, and the alkali metal hydroxide makeup feed stream 138 and water 162 are then added to create the recycle liquid 74, which is then returned to the second stage (sulfur dioxide) aerodynamic reactor 72 to capture additional gaseous pollutants.

The spent solution 78 (from the aerodynamic reactor 72 and aero-coalescer 76 for sulfur oxides removal) is filtered in step 188 and then the liquid 192 is passed into an ion exchange demineralization resin bed 198 for the selective removal of selenium in the form of selenium ions. A portion or all of the selenium may be removed by ion-selective removal through the ion exchange demineralization resin bed 198. The remaining solution is placed through a liquid bypass stream 200 depending on the required or desired removal of selenium, while the cleaned and demineralized solution 205 is returned to the mix tank 140 after the selenium is removed. The selenium is selectively separated from sulfate ions by the additional ion exchange demineralization step 201, and then sent to a selenium recovery step 202. The ion exchange demineralization resin bed 201 is regenerated as the result of the addition of the regenerant solution 203, with the cleaned ion exchange demineralization resin 199 then returned to resin bed 198 for economic reuse after the cyclic regeneration step is completed.

The selenium solution 204 generated from the ion exchange demineralization resin regeneration 201 is then sent for disposal or to further chemical recovery step 202. The spent selenium solution can be evaporated and solidified with lime or other materials and placed in a canister if it is to be disposed of in an approved facility. The alternative is to take the spent solution enriched with selenium and partially concentrate it by evaporation and then recover the selenium for subsequent reuse in the manufacture of electrical or electronic components or solar energy photovoltaic cells or for other economic uses. It may be necessary to convert the selenium to a carbide or oxide compound, or to the purified elemental form to facilitate its recovery and reuse for manufacturing into usable products such as electrical and electronic industry components.

Reference is now made to the chemical metals-recovery and make-up chemical regeneration process 34 as shown on FIGS. 1b and 8. The filtered wash 193 (from the selenium removal prefilter unit 188) and the filtered wash 194 (from the solids prefilter 93) are combined as filter wash stream 195, which is joined with the metals-rich liquid stream 70. The liquid stream 70, 195 is first filtered 31 to remove insoluble particles and then passes through an activated carbon adsorption bed 33 for the removal of any residual elemental mercury and organics.

An alkali metal chloride solution 164 is used as a wash for the prefiltration unit 31 and the wash effluent liquid 165 is then passed to the centrifuge 39 for solids removal. The liquid stream then passes through a precipitation unit 37 where alkali metal sulfate compounds 131 from the mix tank 130 and water 162 (see FIG. 1a) are added to precipitate the soluble mercury chloride compound as mercuric sulfate 133. The liquid stream is then centrifuged 39 to remove the mercuric sulfate and other insoluble solids, which then goes to a water wash 220, then to an acid extraction 222, and to an alkaline extraction 224 system (see FIG. 1a). The soluble liquid from the centrifuge 39 is reconstituted alkali metal chloride 118, which is recycled to the inlet of the chemical recovery system for regeneration of the alkali metal hydroxide solution.

Referring now to the sulfur dioxide chemical-regeneration process shown on FIG. 1b: The sulfur dioxide chemical recovery system employs a thermal decarbonation unit 124 where the unstable alkali metal bicarbonate salts are converted into stable alkali metal carbonate compounds. Carbon dioxide gas 127, liberated by steam heating 128, is then exhausted after condensation of the water vapor as a purified carbon dioxide gas. Furthermore, a portion of the unliberated carbon dioxide remaining in solution may be re-circulated through the operation of the decarbonation unit via line 159 to increase the eventual yield of the carbon dioxide gas as a valuable by-product. Following decarbonation, the sulfur dioxide recovery system employs an oxidation step 126 with hydrogen peroxide 18 (branching into line 146) and air 125 to oxidize the unstable alkali metal sulfite compounds to stable metal sulfate compounds. The oxidized and decarbonated liquid solution containing alkali metal sulfate and carbonate salts from the decarbonation step is then passed to an evaporation-crystallization unit 132 to be concentrated to a solids level sufficient to remove the alkali metal sulfate compounds as a solid 134. The remaining alkali metal carbonate solution 136, water 162, and the alkali metal hydroxide 138 are economically recirculated and added as makeup chemicals and, after passing through a mixing tank 140. These constituents are then returned to the aerodynamic reactor 72 to remove additional sulfur dioxide from the flue gas stream 10 through a series of multiple recycling steps via line 74.

Reference is now made to the related nitrogen oxides chemical-regeneration process shown on FIG. 1b. The nitrogen oxides chemical recovery system is similar to the one for sulfur dioxide removal. The liquid solution 92 removed from the nitrogen oxides aerodynamic reactor system 85, 88 is passed through a prefilter unit 93 with water or alkali metal chloride wash solution 190, and then through a mixing tank 142. The inlet feed wash solution 190 passes to the metals separation and recovery unit 34 through lines 194 and 195. Liquid solution 92 from the mixing tank 142 then passes through line 143 to an oxidation step 144, primarily with hydrogen peroxide solution 146, for conversion of the alkali metal nitrite salts to alkali metal nitrate salts. The oxidized liquid stream, containing the alkali metal nitrates plus alkali metal carbonate and bicarbonate salts, is then passed to a thermal decarbonation unit 148 for decomposition of the alkali metal bicarbonate compounds by steam heating 128 to become the stable alkali metal carbonate compounds.

The carbon dioxide gas 152 from the nitrogen oxides decarbonation is then removed and combined with the exhaust carbon dioxide gas 127 from the sulfur dioxide decarbonation step. Furthermore, a portion of the unliberated carbon dioxide remaining in solution may be re-circulated through the operation of the decarbonation unit 148 via line 149 to increase the eventual yield of the carbon dioxide gas as a valuable by-product. The purified carbon dioxide gas is then dehumidified in condenser 154 and pumped offsite for use in tertiary enhanced oil recovery by injection into oil fields, or for other uses, such as for sequestration via stream 155. This is a part of the comprehensive chemical system for carbon management, capture and utilization of carbon dioxide to form valuable by-products, including methanol, ethanol and ethylene as chemicals or BioFuels. The water removed in step 154 is sent to the water treatment plant 110 via lines 109 and 113 so that it can then be processed for reuse.

The decarbonated liquid solution containing alkali metal nitrate and carbonate salts is then cooled by passage through a refrigeration unit 156. This solution is then passed through an evaporation-crystallization unit 158 for recovery of the alkali metal nitrate compound as crystals 160. The remaining alkali metal carbonate solution 161 is then recycled to the nitrogen oxides aerodynamic reactors 85, 88 after mixing 142 and dilution with added water 162 via line 86. The alkali metal hydroxide feed solution 138 is introduced into mixing tank 142 as chemical makeup to compensate for the nitrogen oxides removed as nitrate salts in the crystallization step 158 in order to maintain chemical recovery system balance.

The alkali metal hydroxide solution 138 added to the sulfur dioxide and nitrogen oxides aerodynamic reactors 72, 85, 88 is produced by the electrolysis of alkali metal chloride solution 164 in electrolysis cell 120 (see FIG. 1a). The electrolysis of the alkali metal chloride salts results in the formation of hydrogen 166 and chlorine 168 gases along with the alkali metal hydroxide solution 138. The hydrogen gas can then either be used for converting ethanol to ethylene in cracking unit 170 or reacted with oxygen to make hydrogen peroxide in unit 172, both of which are makeup chemicals for the pollutant removal system of this invention. The chlorine gas can be reacted with hydrogen to make hydrochloric acid for metals extraction in unit 174, or made into ethylene dichloride by reaction with ethylene in unit 176, which can then be used to produce vinyl chloride monomer 178, and then the polyvinyl chloride plastic material 180. The multiple usages of the recycling and regenerative chemical system of this invention are designed to optimize resource conservation and economic reuse to obtain multiple valuable by-products from the air pollutants captured from the flue gas.

Photolysis of Free Radicals to Facilitate Trace Metals and $NO_x$ Removal

The photolysis unit 14 is designed to produce hydroxyl (OH*) and hydroperoxyl ($HO_2$*) free radicals from hydrogen peroxide and chloro (Cl*) and chloroxyl (ClO*) free radicals from chlorine gas and chlorine dioxide gas. At high temperatures, the free radicals foster rapid oxidation of lower valence oxides of nitrogen to nitrogen dioxide while at lower temperatures these free radicals assist in the reaction of sulfur and nitrogen oxides with alkali metal carbonates and bicarbonates. At high temperatures 500° to 600° C. (930° to 1,110° F.), the free radicals also foster rapid reaction of elemental mercury, mercury vapor, heavy and trace metals such as cadmium, arsenic, germanium, uranium and beryllium to form particulates which may then be captured by the aerodynamic reactor 30. Retention time within the photolysis unit should be at least between 0.1 and 3.0 seconds. At lower temperatures (even as low as 120° C. or 250° F.), the desired reaction may require a longer dwell-time to occur.

Referring now to FIG. 7, the photolysis unit 14 preferably comprises an elongated cylindrical metal section 266 and end plates 268, 270 fastened thereto by a plurality of bolts 271. Preferably, the inner surface of the cylindrical section 266 is polished or otherwise provided with a reflective surface 272. A quartz or glass cylindrical body 274 is sealably affixed to the end plates 268, 270 so as to be substantially concentric with the section 266 thereby defining a central space 276 and an annular space 278 within the cylindrical section 266. Air 19 under pressure from a pump 280 is supplied via air lines 282, which pass through the end plate 268 to the annular space 278. If desired, appropriate air nozzles 284 may be located on the air lines 282 within the annular space 278. Hydrogen peroxide 18 is provided as a liquid stream and enters the annular space 278 and the central space 276 through the end plate 268. An atomizing nozzle 286 is located within the annular space 278 and the central space 276 at the end of the hydrogen peroxide line to atomize the hydrogen peroxide. If desired, a plurality of hydrogen peroxide lines and atomizing nozzles 286 may be provided to more uniformly disperse the hydrogen peroxide within the annular space 278 and the central space 276. Chlorine gas 168 and chlorine dioxide gas 16 are delivered to the photolysis unit 14 through line 56 which passes through the end plate 268. If desired, an appropriate nozzle 288 may be provided to disperse the chlorine and chlorine dioxide within the annular space 278. Of course, multiple chlorine and chlorine dioxide nozzles may be provided, if desired. Water 17 is provided as a liquid stream to the central space 276 via water lines 290 which pass through the end plate 268 and terminate in swirl nozzles 292. While two such nozzles 292 are shown in FIG. 7, it will be appreciated that additional nozzles may be provided, if desired, in order to improve the distribution of the liquid droplets.

A plurality of ultraviolet lamps 294 are located in the annular space 278 and positioned therein by rings 296 which are affixed to the inner surface of the elongated cylindrical section 266. Preferably, grommets 297 placed in orifices formed in the rings 296 secure the ultraviolet lamps 294. If desired, quartz or glass tubes (not shown) may be provided to protect the ultraviolet lamps from the surrounding gases. A power supply 298 provides electric power for the ultraviolet lamps through electric leads 300 along with the fans for air and pumps for water. In operation, the mixture of air, atomized hydrogen peroxide and chlorine and chlorine dioxide gas is subject to photolysis by the ultraviolet light from the lamps 294 so as to produce hydroxyl, hydroperoxyl, chloro and chloroxyl free radicals along with un-reacted air, hydrogen peroxide, chlorine and chlorine dioxide in annular space 278. In like manner, the water and hydrogen peroxide in the central space 276 is subject to photolysis by the ultraviolet light from the lamps 294 so as to produce hydroxyl and hydroperoxyl free radicals and un-reacted water and hydrogen peroxide to be injected into the flue gas.

The photolysis products produced in the central and annular spaces 276, 278 of the photolysis unit 14 together with un-reacted air, water, hydrogen peroxide, chlorine and chlorine dioxide are combined at the outlet of the photolysis unit 14. Free radical product lines 302 extend from the annular space 278 through the end plate 270, while free radical product line 304 extends from the central space 276 through the end plate 270. Free radical products lines 302 and 304 are combined to form free radical line 306. Line 306 feeds into a heater 308 located within the mixing chamber 311. The liquid components of the free radical stream in line 306 are vaporized by the heater 308 and then mixed with the heated air from duct 11 via the air heater 309. The combined air and free radical streams are then injected via duct 24 back into the boiler exit duct 26 at a point where the temperature is still high enough to facilitate chemical reactions.

Preferably, as shown on FIG. 1a, that injection point may be between the air preheater 13 and the economizer 15. In some plants, the economizer may be located upstream of the air preheater. In this event, the injection point preferably is upstream of the economizer to take advantage of the higher flue gas temperature which facilitates the desired oxidation reactions to occur so that the pollutants are then converted into more easily collectible forms.

The primary injection point for the liquid solution containing the free radicals hydroxyl, hydroperoxyl, chloro and chloroxyl may be where the hot gas stream is traveling at a range of temperatures of 500° to 600° C. (930° to 1,110° F.). Preferably, this point is upstream of the economizer for certain types of coals, whereas it may be downstream of the economizer for other types of coals.

The major portion of the oxidation of nitric oxide to nitrogen dioxide occurs at these high temperatures along with the conversion of elemental mercury vapor to mercuric oxide aerosols. Some of the mercuric oxide can then be removed in the downstream electrostatic precipitator or fabric filter as the primary particulate collection device 28, which can also act as a conditioning chamber for particle removal. In addition, at least a portion of the carbon monoxide can be oxidized to carbon dioxide at these elevated temperatures downstream of the air heater. Also a part of the organic vapors and aerosols present as combustion by-products can be converted to carbon dioxide and water vapor to complete the oxidation process.

Exiting from the photolysis unit 14, free radical product lines 302 and 304 are combined to form free radical line 22. The second introduction point for the injection of the free radical-enriched aqueous liquid stream 22 may be at the inlet to the first aerodynamic reactor 30 (see FIGS. 1a, 7, 8) downstream of the primary particulate removal device at temperatures of 135° to 150° C. (275° to 300° F.). At this location, there is additional oxidation of mercury vapor to mercuric oxide and conversion to soluble mercuric chloride aerosols. The mercuric oxide particles can then be removed in the pretreatment section by reaction with potassium chloride or water solutions. The dissolved mercuric chloride in the soluble form is then passed to the metals separation and recovery section 34, where alkali metal (potassium) sulfate 131 from the sulfur oxides removal step is added to precipitate the mercury as the insoluble mercuric sulfate 133. The mercuric sulfate precipitate 133 is then removed and isolated and then either dried and placed in canisters or further processed for recovery to be made into usable by-products.

Separately and alternatively, a dedicated line 23 extending from the central chamber 276 of the photolysis unit 14 distributes only the hydroxyl and hydro-peroxyl free radicals to the injection points three and four, associated with the aerodynamic reactors 72, 85 and 88 (see FIGS. 1a, 1b, 7, 9, and 10).

The third injection point for a selection of free radical-rich liquid solution from the ultraviolet photolysis unit may be on the inlet gas stream of the second aerodynamic reactor system 72 for sulfur oxides removal. If it is desired to add only the hydroxyl and hydro-peroxyl free radicals, this step can be accomplished by using the free radical line 23 as described above. The primary reason for making this injection is to facilitate the completion of the oxidation of nitric oxide to nitrogen dioxide through the provision of sufficient retention time for the gas phase reaction to occur upstream of the subsequent nitrogen oxides aerodynamic reactor 85, 88. However, there will also be the benefit of some gas phase oxidation of sulfur dioxide to sulfur trioxide also occurring to assist in the conversion of sulfite ion to sulfate ion in solution to facilitate the formation of alkali metal (potassium) sulfate fertilizer, as well as to eliminate sulfur trioxide emissions at this stage. In addition, the carryover of hydroxyl free radicals into the liquid phase can also enhance the oxidation of sulfite to sulfate ion in the spent reagent solution in order to facilitate crystallization.

The fourth location for injection of a selection of free radical-enriched solution from the ultraviolet photolysis unit may be at the inlet of the third and fourth aerodynamic reactors 85, 88 for nitrogen oxides removal. If it is desired to add only the hydroxyl and hydro-peroxyl free radicals, this step can be accomplished by using the free radical line 23 as described above. This addition of hydroxyl and hydroperoxyl free radicals makes it possible to complete the oxidation of nitric oxide to nitrogen dioxide so that it can be converted to alkali metal (potassium) nitrate fertilizer. In addition, portions of the carbon dioxide (formed by oxidation of carbon monoxide gas plus organic vapors and aerosols in the gas stream following the air heater plus that coming directly from the boiler combustion zone) can be removed in both the downstream sulfur oxides and nitrogen oxides aerodynamic reactors. This is a part of the comprehensive chemical system for carbon management, capture and utilization of carbon dioxide to form valuable by-products, including methanol, ethanol and ethylene as chemicals or BioFuels.

Metals Recovery and By-Product Reclamation System

Referring now to FIG. 1a, the metals recovery system 116 employs three-stage water washing 220, acidic extraction 222 with hydrochloric acid 175, and alkaline extraction 224 with alkali metal (potassium) hydroxide 138 of the metals separation liquid effluent 35, with entrained solid materials from the first aerodynamic reactor system 30, 32 to separate recoverable metals.

The metals recovery system 231 takes the fly ash 208 and bottom ash 206 solid streams from the coal combustion for processing. The purpose of this processing is to separate the usable metallic and other constituents from the coal ash for recycling and recovery as valuable metallic materials and to remove potentially toxic materials for subsequent isolation and disposal. The unrecovered, non-toxic constituents 210 from the fly ash 208 can be used to make cement, while the unrecovered bottom ash 212 can be made into road base material as usable by-products.

The bottom and fly ash recovery system 231 employs a three step solids-liquid contact system for the treatment of the fly ash and bottom solids streams using water washing 219, hydrochloric acid extraction 112, and alkali metal (potassium) hydroxide extraction 114 in series for metals removal. The effluent liquids 216, 228, 230 (respectively, from the ash wash water system extraction unit 219, and hydrochloric acid extraction step 112, and the alkali metal (potassium) hydroxide extraction step 114 containing the dissolved metallic constituents) altogether comprising the ash metals recovery system 231, are then sent to the metals recovery system 232 for separation into individual metallic constituents, which can then be further processed into useable products at offsite metal smelting and refining plants.

The metals recovery system 232 consists of any or all of four consecutive liquid extraction steps consisting of oxidative extraction 234, nitrate extraction 236, carbonate extraction 238 and organic extraction 240 in series for metals separation into specific individual constituents using chemical solutions readily available from other onsite process streams. Aluminum can be directly recovered from the acidic extraction stream 228 as aluminum chloride for conversion to aluminum oxide by treatment with alkali metal (potassium) hydroxide 138 in unit 250 and subsequent drying 252. The recovered aluminum oxide can then be shipped to an alumina processing facility, or to an aluminum smelter where the aluminum oxide is processed into aluminum metal. Magnesium can be directly recovered as magnesium hydroxide from the alkaline extraction steps 114 and 224 by drying the stream 233 to produce a solid residue.

In addition, uranium can be recovered through a similar two-step sequence 256 from nitrate extraction unit 236 with nitric acid and potassium nitrate as soluble uranyl nitrate in stream 255, which is then converted by precipitation with potassium hydroxide in unit 257 to form insoluble uranium hydroxide solids 258. The uranium hydroxide solids are then dried with heat to form uranium oxide 261 in unit 260, while the liquid is recycled via line 259 to the carbonate extraction unit 238 for reclamation and reuse. The recovered uranium oxide is shipped to a uranium processing facility for conversion into fuel rods for producing electricity in nuclear reactors by a complex multiple step sequence employing milling, conversion, enrichment and fabrication in series.

Other metals can be separately recovered by going through a four-stage extraction by selective consecutive treatment with hydrogen peroxide oxidizing solution 18, 146 and nitrate extraction aqueous solution 160 and nitric acid solution 229 in unit 236. An aqueous solution treatment with an alkali metal (potassium) carbonate feed stream line 139 can be introduced into the carbonate extraction unit 238 for further removal of residual uranium and other metals, and ethanol 119 or other reactants can be introduced into a final organic extraction step 240 for the removal of other metals which can be extracted as organic complexes. The recovered liquids from any or all phases could then be treated through varying ion exchange resins or other steps to remove other metals derived from the coal or any hydrocarbon fuel as may be required. The individual extraction liquid streams can then be further treated for removal and recovery of individual metals onsite or shipped to other locations for smelting or refining or other metals recovery operations into a variety of useable products.

In the metals extraction system 232, the oxidation liquid extraction stream 235 leaves the oxidation unit 234 and enters the nitrate extraction unit 236. The nitrate liquid extraction stream 237 leaves the nitrate extraction unit 236 and enters the carbonate extraction unit 238. The carbonate liquid extraction stream 239 leaves the carbonate extraction unit 238 and enters the organic extraction unit 240. The organic liquid extraction stream 241 leaves the organic extraction unit 240 and enters the return liquids treatment unit 243, where the liquids are treated with alkali metal (potassium) chloride 164. The return liquid wash solids 215 are sent to the waste solids disposal 218, and the un-extracted potash and other liquids 214 returned to the liquid cleaning unit 213. In unit 213, insoluble solids 218 are removed and the reconstituted alkali metal (potassium) hydroxide feed solution 118 is returned to the mixing tank 209. The liquid from the mixing tank 209 is sent to the electrolysis cell 120 for the alkali metal (potassium) hydroxide production. Therefore, the conservation of resources of this invention is also achieved by the recycling of solutions for metal recovery and electrolysis within the chemical regeneration system for economic reuse.

The metals extracted from the oxidation extraction unit 234, the nitrate extraction unit 236, the carbonate extraction unit 238, the organic extraction unit 240 and the return liquids treatment unit 243 are sent to the recovered metals storage facility 244, and thence by line 242 to the appropriate offsite metal smelters, refiners or other recovery plants.

Recycling of Chemical Reagents for the Optimum Conservation of Resources

The partially cleaned flue gas stream 10 following the metals removal step in the first aerodynamic reactor 30 then passes through a second aerodynamic reactor 72 where the sulfur dioxide and sulfur trioxide are removed by absorption into a recycled alkali metal hydroxide-carbonate-bicarbonate solution 74. The sulfur dioxide removal takes place at a reaction temperature of about 50° to 60° C. (120° to 140° F.) with a recycle-flow ratio of about 4.0 to 5.0 of total recycled solution 74 to the makeup feed liquid 138, and with an alkali metal reagent to sulfur oxides (dioxide plus trioxide) concentration ratio of about 2.0 to 3.0, and a liquid pH of about 7.0 to 7.5. The cleaned gas stream then continues to the nitrogen oxides aerodynamic reactor 85, 88 after greater than 99.0% of the sulfur dioxide is removed along with essentially all of the sulfur trioxide. In addition, by this stage between 50 and 75 percent of the carbon dioxide is also captured from the gas stream into the exit reagent liquid system along with the sulfur dioxide at this second stage of the overall flue gas treatment process.

The recycling of the reagent liquid streams used in the processes and provided by and through the chemical generation-regeneration complex designed for optimum conservation of resources and economy is described as follows. The exit liquid stream 78 from the sulfur dioxide reactor system contains a mixture of the alkali metal sulfite and bisulfite compounds as the result of the sulfur dioxide and trioxide removal together with the alkali metal bicarbonate and carbonate salts from the carbon dioxide removal. There may also be a very small amount of alkali metal nitrite and nitrate compounds present in the liquid stream from the sulfur dioxide reactor unit 72 which may also be removed from the flue gas stream. This liquid stream goes to the decarbonation unit 124, where the substantial portion of the carbon dioxide gas 127 is first liberated and removed, with a portion of the unliberated carbon dioxide remaining in solution being recirculated as stream 159 to the decarbonation unit 124 to enhance its follow-on carbon dioxide gas liberation and total yield by repetition.

The recirculated liquid exit stream 196 is transmitted from the mixing tank 140 and fed to a thermal decarbonation unit 124 for stripping with steam 128. The inlet liquid to the decarbonation unit contains alkali metal sulfites and bisulfites plus sulfates along with carbonate and bicarbonate salts. The liquid stream is raised to boiling by heating with steam 128 which causes the alkali metal bicarbonate salts to decompose into alkali metal carbonates and carbon dioxide gas 127. Carbon dioxide gas is evolved and liberated from the decarbonation unit as a wet saturated gas stream, which is passed through a condenser 154 to remove the entrained water vapor and recovered as a purified gas stream 155 from both the sulfur oxides and the nitrogen oxides recovery systems, as a part of this present invention's comprehensive carbon management and carbon dioxide capture system for the conversion into a series of useable by-products which may include methanol, ethanol and ethylene or their derivatives.

The decarbonated liquid stream is then passed to the oxidation unit 126, where the alkali metal sulfite salts are converted to alkali metal sulfates by addition of air 125, where the oxygen reacts with the sulfite ion to produce alkali metal sulfates as soluble salts. The air oxidation step 126 also acts to cause a partial concentration of the spent reagent liquid by evaporation of water into the exhaust gas stream, which is then vented to the atmosphere. The conversion of sulfite to sulfate in conjunction with the alkali metal ions in solution also acts to lower the pH of the spent reagent solution from the air oxidation unit. The exit liquid from the air oxidation unit then passes to the evaporation crystallization unit 132 generally as a thickened slurry for recovery of the sulfate compounds.

Potassium sulfate has a significantly lower solubility in water than potassium sulfite, and has an even lower solubility in potassium carbonate solutions, so that it can readily be removed from the product aqueous media by crystallization. The discharge from the sulfite oxidizer is generally a slurry because of substantial water removal and low solubility of potassium sulfate in the product aqueous media. The slurry may then be cooled and potassium sulfate 134 removed in an evaporator-crystallizer 132. The recovered potassium sulfate 134 is normally centrifuged and removed for drying 245 and packaging 246 as a valuable fertilizer, and the product aqueous media exits from the centrifuge unit. The product aqueous media 136 from the crystallizer is principally potassium carbonate, and may also contain a small amount of potassium sulfate plus any unoxidized potassium sulfite. The aqueous mother liquor is recycled where there is a bleed stream 137 to prevent the accumulation of excessive amounts of non-reactive materials in the reagent solution. Alkali metal (potassium) hydroxide 138 is then added to the mixing tank 140 so that the recycling product aqueous media 136 can compensate for sulfur dioxide component having been removed in the manufacturing of the potassium sulfate product 134, in order to maintain a proper chemical balance.

The remaining partially cleaned flue gas stream (comprising nitrogen oxides and the remaining carbon dioxide) exiting from the sulfur dioxide aerodynamic reactor system 72, 76 then passes to the nitrogen oxides aerodynamic reactor unit 85, which may employ a second aerodynamic reactor 88, into both of which photolyzed hydrogen peroxide via line 23 may be added with an alkali metal hydroxide-carbonate-bicarbonate reagent liquid 86 at the pH of about 9.0 to 9.5, whereby up to 98% of the nitrogen oxides and up to a total of 90% of the remaining carbon dioxide are removed. Cleaned gas (consisting of $N_2$ and $O_2$, water vapor, and possibly trace fugitive emissions) emerges via the duct 96. Chemically, the prior removal of sulfur dioxide in aero-coalescer 76 reduces substantially the quantity of oxidant required, and precludes formation of potassium sulfate during removal and recovery of nitrogen oxides. The recycling potassium hydroxide makeup chemical required for producing the potassium nitrate product may be added from potassium carbonate recycle 86, or from potassium hydroxide 138 electrolytically produced in the electrolysis cell 120 from the potassium chloride feed stream 164.

The spent liquid 92 from the nitrogen oxides ADGC reactors unit 85, 88 then goes to the nitrogen oxides recovery system 141, which is similar to that employed for sulfur dioxide product chemical recovery unit 123. Hydrogen peroxide solution 146 is initially added to the oxidizer unit 144 to facilitate the oxidation of alkali metal nitrites to nitrate salts. The product aqueous media recycle stream 143 comprising regenerated or unconsumed hydrogen peroxide, potassium nitrate and potassium nitrite, potassium carbonate and potassium bicarbonate, passes from mixing tank 142 and is recycled to the oxidizer unit 144 inlet until the concentration of nitrite or nitrate or both reaches a sufficient concentration. Thereafter, at least some of the product aqueous media enters the by-product recovery cycle. Preferably, the product aqueous media to be subjected to by-product recovery passes through the nitrate conversion step where hydrogen peroxide solution has been added to oxidize the nitrite ion to nitrate crystals that will yield nitrate fertilizer as a valuable by-product.

The liquid stream following oxidation of alkali metal nitrites to nitrate salts then passes to a thermal decarbonation unit 148 using steam stripping 128 in a manner similar to that for sulfur dioxide removal. Unliberated carbon dioxide in solution is recycled from the exit via line 149 to maximize alkali metal bicarbonate formation, where the carbon dioxide recirculates through the decarbonation unit to help convert carbonate to bicarbonate, thus lowering the pH to less than about 9.0 and facilitating oxidation of nitrite to nitrate by unconsumed oxidant hydrogen peroxide. Product aqueous media, now rich in potassium nitrate and potassium bicarbonate passes from the thermal decarbonation 148 to a cooling unit 156 and then to the evaporator-crystallizer 158. Thus, a substantial portion of the bicarbonate salts are converted to carbonate salts and carbon dioxide gas by thermal decomposition in the thermal decarbonation unit 148.

Carbon dioxide and water vapor then rise upward and the purified carbon dioxide may be recovered, dried and used elsewhere. It can also be recycled to convert the potassium carbonate to bicarbonate and to facilitate oxidation of potassium nitrite to nitrate. Pressurizing carbon dioxide aids in the conversion of carbonate to bicarbonate and facilitates formation of carbonic acid in the product aqueous media. The oxidation of potassium nitrite to nitrate can proceed faster when carbonic acid is present and carbonate is absent in the liquid stream, which implies a mildly acidic to neutral pH in the liquid phase accompanying the crystallization of potassium nitrate.

The product aqueous media leaving the decarbonation unit 148 contains primarily potassium nitrate and nitrite plus potassium carbonate, and is cooled by a cooling unit 156 to around 10° C. (50° F.), and then travels to the evaporator-crystallizer 158 where potassium nitrate 160 is crystallized. The potassium nitrate crystals 160 are removed from the liquid following centrifuging. The potassium nitrate is then dried 247 and packaged 248. The first portion of the residual alkaline aqueous media stream 161 is recycled back to the mix tank 142. After mixing, it is joined with the recycling of the carbonate-rich aqueous reagent media solution 86, which is being recycled to the ADGC reactor 85, 88 inlets of the nitrogen oxides removal system, along with the addition of potassium hydroxide feed solution 138 and water 162. Some of the recycling aqueous media 161 may be bled into a separate stream 137 to minimize the concentration of inert solids. The second portion of the residual potassium nitrite remaining in the product aqueous media stream 161 can be diverted by an adjustable valve device and be recycled as stream 145 into the oxidation unit 144 either via a direct line, or joining with the addition of oxidant hydrogen peroxide via line 146 also feeding into the oxidation unit 144, in order to maximize the nitrate extraction.

The chemical regeneration and recovery system for the sulfur dioxide, nitrogen oxides, carbon dioxide, mercury and other metals employs a series of cyclic processes for the removal of the air pollutants. The by-product recovery of the alkali metal sulfate and nitrate compounds together with carbon dioxide gas occurs from the flue gas stream directly along with mercury compounds and other metallic constituents. The production of the alkali metal hydroxide solution 138 from the electrolysis of the alkali metal chloride salts 164 makes it possible to generate hydrogen 166 and chlorine 168 gases from the opposite electrodes. It is then possible to produce hydrochloric acid 175 and chlorine dioxide gas 16, plus ethylene dichloride 176 and polyvinyl chloride 180 by-products, as well as hydrogen peroxide 18 and ethylene 121 as makeup chemicals within the overall emission control system complex. It is further possible that alkali metal chloride salts 115 and ethanol 119 would become the only outside makeup chemicals required as raw material feedstock into the system if ethylene is produced onsite at the location where the flue gas treatment is taking place. The multiple usages of the recycling and regenerative chemical system of this invention are designed to optimize resource conservation and economic reuse to obtain multiple valuable by-products. Thus, this is an example of the systematic conservation of resources and the overall regeneration of all the required reagent solutions.

In this present system, a series of cyclic regenerative processes are utilized to remove the individual air pollutants and convert them to usable by-products while recovering the makeup chemicals for reuse. There are separate cyclic chemical recovery processes to handle mercury and metals recovery, sulfur oxides recovery, and nitrogen oxides recovery plus chlorine gas cycling to hydrochloric acid for metals recovery. Moreover, hydrogen gas, is also generated for subsequent utilization to produce hydrogen peroxide and ethylene gas as recycle chemicals to the overall process.

The cyclic regeneration driver and critical step in the entire chemical makeup and recovery system is the electrolysis 120 of the alkali metal chloride salt 164 to alkali metal hydroxide liquid solution 138, plus liberating hydrogen 166 and chlorine 168 gases, with potassium as the preferred alkali metal chloride for the overall removal process, because KCl can be further used to produce the potassium sulfate ($K_2SO_4$), 134, 246 and potassium nitrate ($KNO_3$), 160, 248, both as valuable fertilizers. Makeup potassium hydroxide 138 is conveniently produced in the electrolytic cell 120, where a concentrated solution of potassium chloride 164 is fed to the anode compartment, where it is electrolytically converted to potassium hydroxide 138 in the liquid, with hydrogen 166 and chlorine 168 liberated as gas streams directly at the opposite electrode ends of the electrolysis cell 120. A cationic membrane is used to filter and produce a chloride-free potassium hydroxide product solution 138 for its multiple uses throughout the ensuing processes.

The hydrogen gas 166 from the electrolysis cell 120 can be used to make both ethylene 121 and hydrogen peroxide 18. The hydrogen peroxide may be produced on site from hydrogen plus oxygen, or from air separation unit 171, or from an outside source. Where hydrogen peroxide is made on site, hydrogen gas is reacted with air. Preferably, hydrogen 166 is supplied in whole or in part from the electrolytic cell 120 to make hydrogen peroxide solution 18, 146. The hydrogen peroxide is then photolyzed in the ultraviolet photolysis unit 14 with ultraviolet light 20 to produce hydroxyl and hydroperoxyl free radicals for their multiple uses throughout the ensuing processes. While a portion of the hydrogen is consumed in the production of hydrochloric acid and ethylene cracking, an excess of hydrogen exists which may not be required for the chemical processes involved in the present invention. This surplus hydrogen can be extracted and pressurized as a purified gas or liquid and sold as an additional valuable by-product, such as to an oil refiner for cracking crude oil into products such as gasoline, or to users as in hydrogen fuel cells or as a transportation fuel source.

The chlorine 168 from the electrolysis cell 120 can be beneficially used to produce liquid hydrochloric acid 175 or chlorine dioxide gas 16. The chlorine gas 168 reacting with hydrogen gas 166 directly to produce hydrochloric acid liquid 175 for use in metals extraction operations. The chlorine dioxide gas 16 can be used for the oxidation of nitric oxide to nitrogen dioxide as well as from elemental mercury vapor to mercuric chloride. The major use of the chlorine gas 168 produced in the electrolysis cell 120 is to react it with ethylene gas 121 produced from ethanol 119. Moreover, the chlorine gas can produce a very valuable chain of by-products by reacting with ethylene to produce ethylene dichloride (EDC) 176, as the building block for polyvinyl chloride (PVC) plastic 180 production, through a vinyl chloride monomer (VCM) intermediate 178, where additional ethylene gas 121 must be added at each step. There exists a market for such by-products because they are direct substitutes for the same chemicals manufactured out of the much more expensive raw material feedstock supplied by the petroleum industry.

Carbon Capture and Management System, with Hydrogen Gas Production

Figure 11:
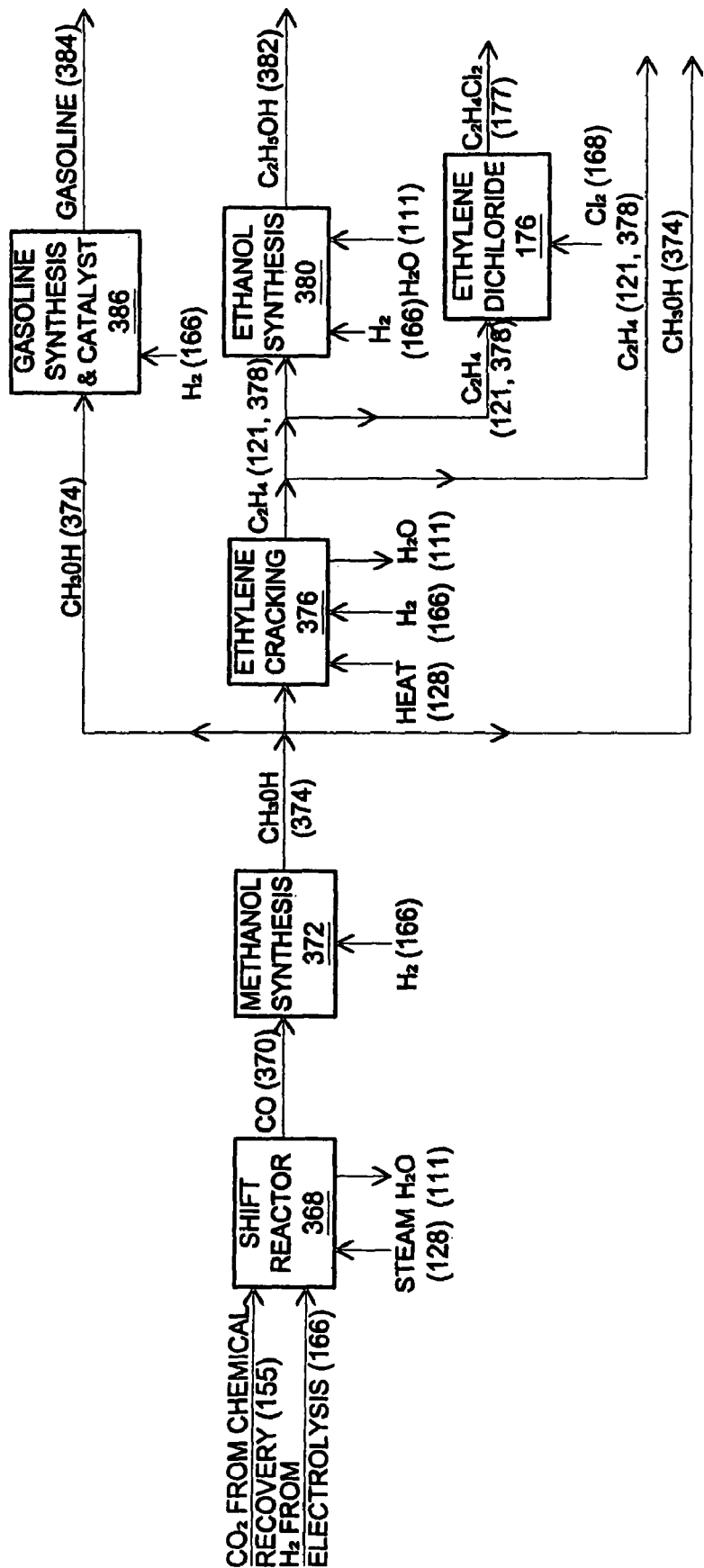
FIG. 11 shows a flow-chart of a supplement to the system of FIGS. 1a and 1b, by which methanol, ethanol, ethylene, ethylene dichloride and BioFuels can be synthesized from hydrogen, chlorine and carbon dioxide.

The carbon dioxide ($CO_2$) content of combustion gases may be in the range of about 5% to about 60% of the volume of the combustion gases. It is now widely believed that carbon dioxide contributes significantly to global warming. Efforts have been made to limit the release of carbon dioxide to the atmosphere and government regulations may soon require further limitations. The present invention is uniquely designed toward the management of carbon dioxide since the decarbonation steps of both the sulfur oxides and nitrogen oxides chemical recovery process liberate carbon dioxide as a pure gas, which can then be recovered as a harvested gas or pressurized into a liquid. Most of the remaining carbon appears as an alkaline metal carbonate, which is recycled to the sulfur and nitrogen oxides reactors. The combination of using the alkali-carbonate-bicarbonate solution as a management tool for carbon content and carbon values is a novel benefit of this invention. Where there is an excess of stored carbon values in the solution, the additional alkali metal carbonates and bicarbonates may be produced in a form sellable to users or for converting into synthetic fuels (as shown in FIG. 11). This is a part of the comprehensive chemical system for carbon management, capture and utilization of carbon dioxide to form valuable by-products. As a result of this present invention only trace amounts of carbon oxides and other constituents may become fugitive and escape up the stack as an exhaust gas.

Figure 10:
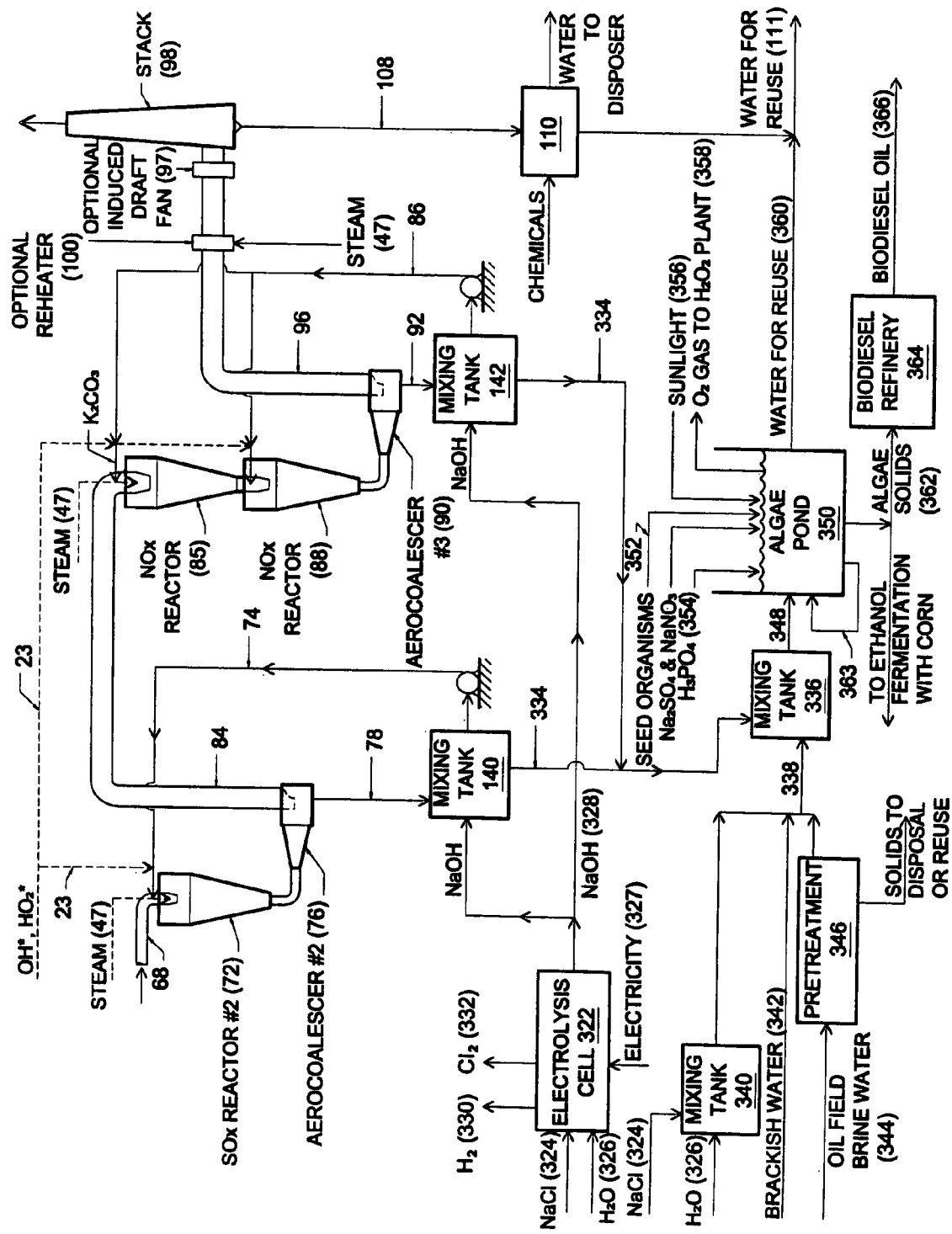
FIG. 10 shows a flow-chart of a supplement to the system of FIGS. 1a and 1b, by which BioDiesel fuel oil may be produced from algae synthesis and fermentation.

A very valuable by-product is carbon dioxide gas which is produced by liberation from the alkali metal (potassium) bicarbonate solutions during the thermal decarbonation with steam and heat during the sulfur oxides and nitrogen oxides chemical recovery steps. The carbon dioxide is liberated from solution in each case by heating the liquid recycling streams of the alkali metal carbonate-bicarbonate from the respective sulfur oxides and nitrogen oxides chemical recovery processes to boiling conditions. The alkali metal (potassium) bicarbonate in each stream then decomposes to liberate carbon dioxide from solution as a saturated wet gas 127, 152 plus alkali metal (potassium) carbonate. The carbon dioxide is then passed through a condenser 154 for dehumidification and then exited as a product for use in tertiary enhanced oil recovery and other applications such as enhanced vegetable growth in greenhouses, or to grow algae with photosynthesis for making synthetic or BioDiesel fuels (as shown in FIG. 10).

The normal process operating mode is to utilize potassium chloride (potash) as the incoming chemical makeup solution so as to be able to produce the valuable potassium sulfate ($K_2SO_4$) and potassium nitrate ($KNO_3$) as fertilizers.

The carbon dioxide ($CO_2$), which is recovered as a purified gas is a by-product having considerable value, either for regulatory sequestration or for commercial purposes. A portion of the carbon dioxide gas, which is recovered can be used for tertiary enhanced oil recovery by injecting with water flooding into nearby oil fields to increase rock porosity and to reduce fluid density. The result of the carbon dioxide injection is that the crude oil molecules in the porous layers then have more room to flow and can flow more easily from the formation. Greater quantities of oil can then be recovered, thus resulting in improved crude oil yields, increasing field reserve estimates, and in extending existing field lifetimes. The use of carbon dioxide as an agent, either together with steam injection or by itself, for tertiary enhanced oil recovery is of great economic benefit for the oil market in increasing potential energy resources.

The carbon dioxide can also be introduced either separately or together with the incoming air into hydro-aeroponic greenhouses to enhance production of agricultural crops such as vegetables, fruits and young trees. It is then possible to extend the growing season of crops and agriculture into cold climates with artificial lights using the electricity from the power plant to assist the carbon dioxide from the power plant. The carbon dioxide by-product can also be used to make ethanol, methanol, ethylene, synthetic fuels, and other chemicals, or be used to grow algae with photosynthesis for making BioDiesel fuels. In short, the invention with its ability to regulate and control the release of carbon dioxide from solution contains a novel method of virtually total carbon capture, carbon reuse, and carbon management, and thereby to minimize the escape of carbon dioxide into the atmosphere, and to produce a series of very valuable carbon-derivative by-products.

The hydrogen gas 330, 166 is an additional product of the electrolysis of the alkali metal (potassium) chloride raw material. A portion of the hydrogen gas is utilized for the production of hydrogen peroxide ($H_2O_2$) by reaction with oxygen as the chemical agent for oxidizing nitric oxide to nitrogen dioxide to facilitate its removal along with elemental mercury to mercuric chloride in conjunction with chlorine. An additional portion of the hydrogen gas is used to react with chlorine to produce hydrochloric acid (HCl) for extracting aluminum and other valuable metals from the ash extracts from the coal. Another part of the hydrogen gas produced by electrolysis is consumed by reaction with ethanol to form the ethylene gas ($C_2H_4$), which is then combined with a part of the chlorine gas to produce the ethylene dichloride ($C_2H_4Cl_2$) intermediate as the building block for polyvinyl chloride plastics manufacture. Furthermore, it is possible that any of the otherwise unused hydrogen gas can then be sold offsite as a future transportation fuel or for use as a cracking and reforming chemical agent at any nearby oil refineries or for other purposes, such as a transportation fuel.

Alternative Alkali Metal Reagents for Producing Other By-Products

There may be certain cases where the potassium chloride supply may not be readily available, or the potassium-based fertilizer by-products generated from the practice of the invention may not be suitable in appropriate quantities for the existing markets. For such a situation, it may be advantageous to use another chemical base for the electrolysis in place of potassium chloride (potash). Another alternative raw material to potash is the use of the sodium chloride salt (NaCl), which produces the less valuable sodium sulfate ($Na_2SO_4$) and sodium nitrate ($NaNO_3$) as industrial chemicals.

For some cases where high carbon dioxide removal efficiencies at lower cost are required for either regulatory or for economic reasons, then it would be possible to use either a combined potassium and sodium chemical base, or even to replace the potassium-based reagent material for the electrolysis process by the less expensive and more readily available sodium-based salt.

In another alternative case, some of the aerodynamic reactors of the invention can utilize the potassium base chemicals to achieve sulfur oxides and nitrogen oxides removal, while an added aerodynamic reactor stage to remove carbon dioxide can utilize the sodium base chemicals. Such an arrangement will require separate electrolysis cells and chemical recovery systems for different alkali metal solutions, where the use of dual sodium-and-potassium base raw materials is practiced. The dual-chemical base arrangement adds to the flexibility of operation of the present invention for situations, especially where large quantities of carbon dioxide are needed for the tertiary enhanced oil recovery in existing oil fields or to meet future regulatory standards such as "zero emission" condition.

An example of a practical utilization of the sodium base chemical recovery system is shown in FIG. 10, which is a process flow diagram for the production of BioDiesel oil from algae by means of photosynthesis. It will be understood that FIG. 10 supplements FIGS. 1a and 1b, where the sulfur dioxide aerodynamic reactor 72 and the nitrogen oxides aerodynamic reactors 85, 88 are operated with sodium carbonate-hydroxide reagent solutions. Referring particularly to FIG. 10, flue gas stream 10 from the first aerodynamic reactor 30 and the aero-coalescer 32 enters the second aerodynamic reactor 72 via duct 68 and passes through the aero-coalescer 76, which separates a liquid portion 78 comprising a sodium bicarbonate and carbonate solution with sulfite and sulfate constituents from sulfur oxides, from a gaseous portion comprising carbon dioxide and monoxide, nitrogen oxides, air and water vapor.

The remaining flue gas in duct 84 from the aero-coalescer 76 then continues onward and passes through the third and fourth nitrogen oxides aerodynamic reactors 85, 88 and aero-coalescer 90 which separates the liquid and gaseous components of the exhaust gas stream. The liquid component comprising sodium carbonates and bicarbonates with nitrite and nitrate constituents is sent to the nitrogen oxides chemical recovery mixing tank 142 via line 92. The exhaust gas in duct 96 comprising air, water vapor and a trace amount of fugitive carbon oxides, principally would be carbon dioxide if any found, is directed to the stack 98 as essentially clean air.

In FIG. 10, the sodium hydroxide required as the makeup chemical is produced by electrolysis of a salt solution in electrolysis cell 322. Salt (NaCl) 324 and water 326 together with electricity 327 are inputted to the electrolysis cell 322. As a result, the electrolysis cell 322 produces sodium hydroxide 328, hydrogen gas 330 and chlorine gas 332. The sodium hydroxide 328 is delivered to the mixing tanks 140, 142 while the hydrogen gas 330 and chlorine gas 332 may be used elsewhere in the process as herein before described or sold as by-products. The sodium hydroxide is then used as the makeup chemical for sulfur dioxide and nitrogen dioxide removal from the flue gas stream.

The spent reagent liquid 334 may be recirculated from the mixing tanks 140, 142 of the respective sulfur oxides and nitrogen oxides chemical recovery systems into mixing tank 336 where it is mixed with additional salt water solution 338. The salt water solution 338 may be provided from any convenient source, such as a direct mixture of salt 324 and water 326 in a tank 340 or a local supply of brackish water 342. The liquid effluent waste brine water 344 from an oilfield can also be used as an alternative source of brine solution after being treated in an oil-water flotation separation unit 346 to remove oil from the brine water 344. The recovered oil can then be reclaimed for reuse while the cleaned salt water can then be used to produce algae by photosynthesis so that it can be made into BioDiesel fuel.

The solution 348 comprising sodium carbonates and bicarbonates and sodium chloride serves as the principal feed to an algae pond 350. In order to promote rapid growth of algae in the pond 350, sodium sulfate and sodium nitrate, both produced as by-products by the process of the present invention, are added to the pond directly or, if desired, to the mixing tank 336. In addition, appropriate seed organisms 352, such as yogurt or yeast, may be added to promote algae growth. Finally, phosphoric acid ($H_3PO_4$) 354 may be added to the pond 350. The phosphoric acid 354 is not already available within the process of the present invention and, therefore, must be provided from commercial or other sources.

Within the pond 350, the application of sunlight or artificial light 356 results in photosynthetic reactions, which consume carbon dioxide and produce algae and release oxygen 358. Excess water 360 from the pond 350 may be recycled to the mixing tank 336 or reused elsewhere 11 1. A portion of the algae solids may be recycled to the algae pond 350 via line 363 to promote more rapid growth of algae. The remainder of the algae solids 362 may be sent to a BioDiesel oil refinery unit 364 to produce BioDiesel oil 366, a valuable transportation fuel. The BioDiesel oil refining process is well-known to the art and need not be described here in detail.

Algae can be produced by photosynthetic reactions to form either oxygen or hydrogen gases along with algae solids. For liquid feed streams where sulfur in the form of sulfate compounds are included with nitrate, phosphate and other nutrients, the photosynthetic reactions produce algae cells plus oxygen gas from the reaction of carbon dioxide and water in the presence of sunlight. For liquid feed streams containing nitrate, phosphate and other nutrients plus organic waste materials, the photosynthetic reactions can produce algae cells plus hydrogen gas in place of oxygen in the presence of sunlight when sulfur compounds are absent.

Carbon Capture and Producing Methanol, Ethanol, BioFuels, Ethylene and Their Derivatives It will be appreciated that, in accordance with the present invention as supplemented by the production of algae, almost all of the carbon dioxide generated by the combustion of hydrocarbon fuels in a power plant or other industrial process is either captured or consumed so as to become valuable commercial by-products, and is not available to escape into the environment, except as fugitive traces. The carbon dioxide captured from the flue gas also can be converted into ethanol, methanol or ethylene by the reaction with hydrogen from the electrolysis of the potassium (or sodium) chloride to potassium (or sodium) hydroxide as the absorbing solution for the sulfur dioxide, nitrogen dioxide and carbon dioxide from the power or industrial plant flue gas stream. The result is that nearly the entire balance of the carbon dioxide can be converted into the useable by-product chemicals (methanol, ethanol, ethylene, and all of their derivatives), which can be used as industrial chemical feedstocks or as transportation fuels. In short, the present invention describes, as follows, a novel pathway for making hydrocarbon fuels and derivative chemicals from captured flue gas comprising carbon dioxide, organics, hydrogen, or chlorine as direct substitutes for feedstock chemicals supplied by the petroleum industry. Such unique method of this invention is only enabled by the application of aerodynamic science with molecular surface chemistry and conventional chemistry, the combination of which is hitherto not yet known or practiced.

Referring to FIGS. 1a, 1b and 11, the carbon dioxide gas is collected from the flue gas streams of the power or industrial plant from the sulfur dioxide and nitrogen dioxide chemical recovery systems 123 and 141. This combined carbon dioxide gas stream 155 from the water vapor condenser 154 is brought to the inlet of a shift conversion reactor 368, where hydrogen gas 166 from the electrolysis cell 120 are reacted together with steam 128 to form carbon monoxide and water vapor in the synthesis according to the following chemical reaction:

$$CO_2 + H_2 \rightarrow CO + H_2O$$

The synthesis gas 370 comprising carbon monoxide can then be reacted with hydrogen gas 166 across a chromium oxide—zinc oxide catalyst 372 to produce liquid methanol 374 according to the following chemical reaction:

(Methanol)

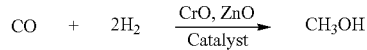

The methanol 374 produced thereby can then either be used directly as an industrial chemical or passed through a heating unit or cracking furnace 376 to produce ethylene gas 378 by heating with steam or gas 128 and hydrogen gas 166 (to retain a reducing atmosphere) according to the following reaction:

(Ethylene)

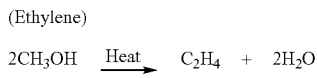

The ethylene gas 378 (which can be produced from methanol) can then be reacted with chlorine gas 168 from the electrolysis cell 120 to produce ethylene dichloride 177 in reactor unit 176 according to the following chemical reaction:

$$C_2H_4 + Cl_2 \rightarrow C_2H_4Cl_2 \quad \text{(Ethylene Dichloride)}$$

The ethylene dichloride (EDC) 177 can then be reacted with additional ethylene gas 121 to produce vinyl chloride monomer 179 and then further reacted with additional ethylene gas 121 to produce polyvinyl chloride plastic (PVC) 180, while the unused or surplus ethylene gas can be transmitted elsewhere and also can be used to manufacture other petrochemicals. Ethylene 121, 378 can also be reacted with water 111 and hydrogen gas 166 (to maintain a reducing atmosphere) in ethanol synthesis reactor 380 to produce ethanol liquid 382, which can then be used to manufacture chemicals or used as a transportation fuel source according to the following chemical reaction:

$$C_2H_4 + H_2O \rightarrow C_2H_5OH \quad \text{(Ethanol)}$$

In addition, methanol or ethanol can be directly converted to BioFuel (and Fuel Feedstock, such as components to making gasoline 384), and can be assisted by passage over a catalyst 386, such as zeolite.

Production of Air from Hot Combustion Gases (Flue Gas)

As demonstrated in the description of the invention up to the present point, the process of the invention first separates such metals (other than selenium) and particulates as may be present in the hot combustion gas in an aerodynamic reactor and isolates them for recovery or disposal as may be most economical. Then, the process removes selenium (if present) for recovery or disposal and the sulfur oxides in the form of a solid alkali metal sulfate together with a portion of the carbon dioxide to be released as a pure gas (and to be reclaimed and reused) from the decomposition of an alkali metal bicarbonate. Finally, the process removes the nitrogen oxides in the form of a solid alkali metal nitrate together with a portion of the carbon dioxide to be released as a pure gas (and to be reclaimed and reused) from the decomposition of an alkali metal bicarbonate.

Having removed the metals, particulates, sulfur oxides, nitrogen oxides and carbon dioxide from the combustion gas, the exit gas comprises oxygen, nitrogen, water vapor, and, possibly, trace amounts of other fugitive constituents. As this composition is essentially air (as is commonly and universally understood), the process of the invention may appropriately be defined as a process for producing air from combustion gases. In short, this process of the invention produces clean air from dirty flue gas.

Process for Maximizing Carbon Dioxide Recovery and Production

While the process of the present invention has been described up to the present point in its application to hydrocarbon fuel boilers, such as for power generating or industrial process co-generating plants or maritime boiler and turbine-engine operations, it may also be applied to maximizing carbon dioxide recovery and production with a few modifications, such as for municipal or industrial incineration plants, or for petroleum refinery process off-gases, or for agricultural fermentation and process exhaust gas (e.g. carbon sequestration), resulting in comprehensive flue-gas recapture and management. Reference is now made to FIGS. 12a and 12b which show a re-arrangement and modification of the flow diagrams shown on FIGS. 1a and 1b. For clarity and consistency, parts performing the same or a similar function in both sets of Figures will be identified by the same indicators followed by "A" on FIGS. 12a and 12b.

In FIG. 12a, the boiler 12A is fed with solid waste 400 and, if necessary, auxiliary fuel 402, such as natural gas, oil, or powdered coal, and air 19A. Of course, the solid waste need not be used in many processes. The hot flue-gas 10A passes through a pre-heater 13A, duct 26A, economizer 15A and primary collection device 28A. A photolysis unit 14A employing ultraviolet light 20A is fed by air 19A, water 17A, hydrogen peroxide 18A and chlorine and chlorine dioxide 56A and produces hydroxyl, hydroperoxyl, chloro and chloroxyl free radicals which, together with heated air 11A, are delivered to the duct 26A via line 24A. Bottom ash 206A and fly ash 208A, respectively from the boiler 12A and primary particle collection device 28A are delivered to the metals recovery system 231 for further treatment as shown on FIG. 1a.

The hot flue-gas 10A leaves the primary particle collection device 28A through duct 38A and enters the first stage aerodynamic gas cleaning reactor 30A through entry duct 36A. Aerodynamic reactor 30A is driven by steam 47A, air or a gas and is supplied with an alkali metal chloride solution from line 164A, hydroxyl, hydroperoxyl, chloro, and chloroxyl free radicals from line 22A and chlorine and chlorine dioxide gas via line 56A. Within the reactor 30A, the particulate, metals and aerosols are encapsulated in liquid droplets as heretofore described. The liquid droplets are separated from the gas stream in the gas/liquid separator 32A as heretofore described and leave the gas/liquid separator 32A via line 70A while the partially cleaned gas leaves the gas/liquid separator 32A through duct 68A and enters the second stage aerodynamic gas cleaning reactor 72A through entry duct 36A.

Aerodynamic reactor 72A is driven by steam 47A, air or a gas and is supplied via line 74A with an alkali metal hydroxide, carbonate-bicarbonate solution and via line 23A with hydroxyl and hydroperoxyl free radicals. Within the reactor 72A, the sulfur dioxide and some of the carbon dioxide contained in the flue-gas 10A are encapsulated in liquid reaction products as heretofore described and the gas/liquid mixture delivered to the second stage gas/liquid separator 76A. The liquid droplets are separated from the gas stream in the gas/liquid separator 76A as heretofore described and leave the gas/liquid separator 76A via line 78A while the partially cleaned gas leaves the gas/liquid separator 76A through the duct 84A and enters the third stage aerodynamic gas cleaning reactor 85A through entry duct 36A.

Aerodynamic reactor 85A is driven by steam 47A, air or a gas. If desired, additional quantities of the hydroxyl and hydroperoxyl free radicals may be fed to reactor 85A through line 23A while the reactor is supplied with an alkali metal hydroxide, carbonate-bicarbonate solution via line 86A. Within the reactor 85A the nitrogen oxides and another portion of the carbon dioxide contained in the flue-gas 10A are encapsulated as reaction products as heretofore described. The liquid droplets formed in reactor 85A are separated from the flue-gas 10A in gas/liquid separator 90A as heretofore described and leave gas/liquid separator 90A via line 92A while the more fully cleaned gas leaves the gas/liquid separator 90A through exit duct 407.

The alkali metal hydroxide, carbonate-bicarbonate solution 74A is introduced into reactor 72A at a pH level of about 7.0 to 7.5 where it preferentially reacts with the sulfur dioxide, while the alkali metal hydroxide, carbonate-bicarbonate solution 86A is introduced into the reactor 85A at a pH level of about 9.0 to 9.5 where it reacts preferentially with the nitrogen oxides. Thus, the sulfur dioxide is captured in reactor 72A while the nitrogen oxides are captured in reactor 85A. A portion of the carbon dioxide is captured in each reactor in the form of an alkali metal carbonate-bicarbonate solution.

The more fully cleaned flue-gas in exit duct 407 enters the fourth stage aerodynamic gas cleaning reactor 404 through entry duct 36A. Aerodynamic reactor 404 is similar in design and operation to reactors 30A, 72A and 85A as heretofore described. It is driven by steam 47A, air or a gas and fed with an alkali metal hydroxide carbonate-bicarbonate solution 408. Within the reactor 404 the remainder of the carbon dioxide and any traces of sulfur dioxide and nitrogen oxides are captured in liquid form as carbonates-bicarbonates, sulfites and nitrites at a pH of about 10.0 to 11.0 and separated in gas/liquid aero-coalescer separator 406. The cleaned gas leaves the aero-coalescer separator 406 through duct 96A, passes through an optional re-heater 100A heated by steam 128A, and an optional induced draft fan 97A and into stack 98A. Water 108A recovered from the stack 98A is treated and reused as heretofore described.

The chemical generation-regeneration system employed for FIGS. 12a and 12b is similar to that employed in FIGS. 1a and 1b. First, an alkali metal chloride salt feed solution 115A (preferably potash or potassium chloride) and water 17A are mixed in alkali metal chloride mixing tank 209A to form an alkali metal chloride feed solution 164A. A portion of the alkali metal chloride solution 164A is directed to the alkali metal chloride electrolysis cell 120A where the alkali metal hydroxide 138A is formed along with hydrogen gas 166A and chlorine gas 168A. As shown in FIGS. 1a and 1b, the hydrogen gas 166A and chlorine gas 168A are used, along with oxygen from an air separation plant 171, to form hydrogen peroxide 18A, hydrochloric acid 175A and chlorine dioxide 16A and 56A required at various points in the process.

The alkali metal chloride solution 164A is delivered to reactor 30A while the spent liquid 70A from gas/liquid aero-coalescer separator 32A is returned to the metals recovery-regeneration system 34 shown in FIG. 1a.

The alkali metal hydroxide solution 138A is also delivered to mixing tanks 410, 412 and 414. From mixing tank 412 the recycle solution 74A comprising the alkali metal hydroxide and alkali metal sulfites, nitrites and carbonates-bicarbonates is cycled to the reactor 72A, while the spent solution is returned to the mixing tank 412 after passing through the filter 418. A portion of the solution in the mixing tank 412 is withdrawn through line 416, and, sequentially, passed through thermal decarbonator 420, oxidizer 422, and evaporator-crystallizer 426. The liquid effluent 428 is recycled to the mixing tank 412, while a bleed stream 429 is employed to minimize the concentration of inert solids. In the thermal decarbonator 420, steam 128A is used to break down the bicarbonates to carbonates and liberate the saturated carbon dioxide gas 430. As shown on FIG. 12b, the saturated carbon dioxide gas 430 may be purified by condensing the water it contains in condenser 462. In the oxidation reactor 422, hydrogen peroxide 146A is used to convert the alkali metal sulfites and nitrites to alkali metal sulfates and nitrates. Thereafter, the solution is evaporated with steam 128A and crystallized in the evaporator-crystallizer 426. The output of the evaporator-crystallizer 426 is alkali metal sulfate crystals 432 which may be dried, packaged and sold as a fertilizer as shown on FIG. 1b.

The alkali metal hydroxide 138A delivered to mixing tank 410 is fed as stream 86A to reactor 85A while the spent solution from the gas/liquid aero-coalescer separator 90A is returned via line 92A to the mixing tank 410 after passing through filter 450. A portion of the solution in mixing tank 410 is withdrawn through line 452 and then passed, sequentially, through oxidizer 454, thermal decarbonator 456, cooler 458 and evaporator-crystallizer 460. Steam 128A is supplied to the thermal decarbonator 456 to liberate the saturated carbon dioxide gas 430. Hydrogen peroxide 146A is supplied to the oxidizer 454 and steam 128A is supplied to the evaporator-crystallizer 460 to produce alkali metal nitrate crystals 434 which may be dried, packaged and sold as a fertilizer as shown on FIG. 1b. The effluent liquid stream from the evaporator-crystallizer 460 is returned to mixing tank 410 via line 464, while inert solids are removed through bleed stream 466 to avoid undesirable accumulation.

The alkali metal hydroxide 138A delivered to mixing tank 414 is fed as stream 408 to reactor 404 while the spent solution from the gas/liquid aero-coalescer separator 406 is returned to the mixing tank 414 via return line 436 and filter 440. A portion of the solution in mixing tank 414 is withdrawn through line 438, passed through acidulating reactor 470 supplied with hydrochloric acid 175A and thence to thermal decarbonator 442, where it is heated by steam 128A to liberate the saturated carbon dioxide gas 430. The hydrochloric acid 175A is added into the acidulation reactor 470 to react with the alkali metal carbonate-bicarbonate solution feeding from line 438 in order to favor the formation of the less chemically stable bicarbonate ion at the expense of the more stable carbonate ion, so that the preferential liberation of carbon dioxide gas from the liquid phase can occur. The saturated carbon dioxide gas 430 may be purified by condensation in condenser 462. The effluent liquid stream 446 is recycled to mixing tank 414 while a bleed stream 448 is employed to minimize the concentration of inert solids.

It will be appreciated that the system shown in FIGS. 12a and 12b is another example of the comprehensive carbon management system of the present invention as applied to the problem of controlling the pollution generated by industrial processes. Specifically, the purified carbon dioxide resulting from this invention may be used to produce fuels as shown on FIGS. 10 and 11, tertiary recovery in oil fields and as a commercial end product.

Solution for Burning High-Sodium Hydrocarbon Fuel, such as Lignite and Other Low Rank Coals The burning of high sodium content coals, such as the lignite coals from North Dakota, Texas and other areas, can cause considerable operating problems because of the presence of elevated concentrations of sodium in the ash residues. The operating problems which can result from having elevated levels of sodium in the ash as with lignite coals can include boiler fouling and plugging, or the undesirable coating of heat transfer surfaces with reduced thermal efficiencies. In addition, there can be carryover of fine particles escaping capture by slipping through the electrostatic precipitators or bag house filters that are commonly used for particulate collection, because of excessively low ash resistivity levels (slipperiness) associated with high sodium levels in the coal. As a result, it is frequently difficult to properly and efficiently burn lignite and other coals with high sodium contents in conventional combustion equipment.

The conventional combustion of lignite coals through pulverized firing occurs where the coal is ground into fine particles and burned by suspension in an air stream. The result is that the sodium present in the ash initially melts upon burning of the organic materials in the coal and then recondenses and solidifies as fine aerodynamic particles which are entrained into the flue gas to be subsequently deposited unavoidably on the boiler tubes or heat transfer surfaces. The partially melted sodium ash particles can then deposit and stick onto surfaces so as to adhere or cement to surfaces or to other particles, and be difficult to remove by conventional soot blowing operations. In addition, such fine sodium ash particles can be easily deposited onto and line the collection plates of electrostatic precipitators, and then be re-entrained into the gas stream because of their low resistivity levels, and then aerodynamically escape into the atmosphere as a visible plume.

One way to alleviate the above problems with high sodium contents in such lignite coal ash is to utilize cyclone firing in place of pulverized firing in boilers. In the case of cyclone firing, the coal is ground into small but not fine particles and burned in a primary cylindrical tube with air before entering the main secondary combustion chamber, instead of being ground into a fine powder suspension and injected with air directly into the main combustion chamber. The two-step cyclone firing process allows for high volatile coals to be vaporized before burning and the high sodium contents in coals to be pre-melted before burning. Therefore, cyclone firing allows for the volatile gases and vapors to be initially and rapidly burned with a high heat release into the primary combustion tube, while the slower burning of the fixed carbon occurs mainly in the secondary combustion chamber. The high rate of heat release in the combustion tube melts the sodium and other coal ash materials. Therefore, the molten discharge can be removed from the bottom of the boiler as a liquid slag for easier removal and subsequent recovery, instead of being entrained into the exit flue gas as with pulverized coal firing.

Cyclone firing makes it possible to efficiently burn highly volatile lignite coals with high sodium ash contents with a minimum of operational difficulties through high temperature precombustion in a confined cylindrical tube with centrifugal air mixing. Cyclone firing makes it possible to rapidly burn the volatile light organic compounds in the lignite coal while rapidly evaporating the moisture into water vapor and melting the ash into a fused liquid stream to be removed from the bottom of the boiler. As a result, there is a significant reduction in the fly ash carryover in the flue gas stream entering the downstream particle collection device thereby reducing its total workload and maintenance.

However, the high temperatures associated with cyclone firing of lignite coals in the primary combustion tubes also results in the generation of significant amounts of nitrogen oxides which are much greater than the emissions from comparable pulverized coal firing. These inherently higher nitrogen oxides emissions associated with traditional cyclone firing of lignite and other low rank coals have led to its being virtually outlawed by regulatory agencies in order to suppress the generation of nitrogen oxides pollution as a part of protecting the environment. On the other hand, the innovative process of the present invention for nitrogen oxides elimination will make it possible to reincarnate cyclone firing as a suitable and desirable technology for burning high sodium and high volatile content lignite and other low rank coals with minimal operating problems. The present invention effectively removes and eliminates the nitrogen oxides pollution previously so emitted, and it efficiently converts them into usable potassium nitrate fertilizer by-products in such great amounts so as approaching near total recovery of available nitrogen compounds. There should be no detectable harmful $NO_x$ emitted from the stack subsequently. Therefore, it is a novel and complementary solution to using the known method of cyclone firing and making it superior to the conventional pulverized coal firing.

The terms and expressions which have been employed are used as terms of description and not of limitation and there is no intention, in the use of such terms and expressions, of excluding any equivalents of the features shown and described or portions thereof, but it is recognized that various modifications are possible within the scope of the invention claimed.

Although not wanting to be bound by any theory, the chemical reactions involved are given in Appendix 2.

APPENDIX 1

IDENTIFICATION NUMBERS

4 Coal Fuel to Boiler
6 Liquid Ultraviolet Photolysis Section
8 Gaseous Ultraviolet Photolysis Section
9 Chloro and Chloroxyl Free Radicals
10 Hot Flue Gas Stream
11 Air Duct feeding into Free Radicals Mixing Chamber
12 Boiler (Coal-Fired)
13 Air Preheater Exchanger
14 Ultraviolet Photolysis Unit
15 Economizer Heat Exchanger
16 Chlorine Dioxide Gas Stream
17 Water Liquid Stream
18 Hydrogen Peroxide Liquid Stream
19 Ambient Air Source
20 Ultraviolet Light
22 Chloro, Chloroxyl, Hydroxyl and Hydroperoxyl Free Radicals Feed Line to First Stage ADGC Reactor
23 Hydroxyl and Hydroperoxyl Free Radicals Feed Line to Later Stages ADGC Reactors
24 Duct containing Hot Air Mixed with Free Radicals Stream from Photolysis Unit
26 Boiler Exit Duct
28 Primary Particle Collection Device (usually ESP)
30 First Stage Aerodynamic Gas Cleaning (ADGC) Reactor (or Metals Cleaning ADGC Reactor)
31 Metals Separation Prefilter
32 First Aero-Coalescer Separator
33 Activated Carbon Adsorber
34 Metals Separation and Recovery/Regeneration Process Unit
35 Metals Separation Unit Effluent Liquid
36 Aerodynamic Gas Cleaning Reactor Entry Duct
37 Chemical Precipitation Unit
38 Particle Collection Device Exit Duct
39 Multiple Stage Centrifuge
40 Mixing/Reaction Chamber
42 Subsonic Nozzle
43 Manifold associated with Supersonic Nozzle
44 Supersonic Nozzle
45 Spray Nozzle for Supersonic Nozzle
46 Supersonic Free Jet
47 Steam/Air Injection Drive Media for ADGC Reactors
48 Subsonic Nozzle Throat
49 Manifold associated with Subsonic Nozzle
50 Subsonic Free Jet

APPENDIX 1

51 Spray Nozzle for Subsonic Nozzle
52 Mixing/Reaction Chamber Decreasing or Converging Cross Section
54 Nozzle Apertures
56 Chlorine and Chlorine Dioxide Entry Line
58 Alkali Metal Chloride Entry Line for Metals Reactor
60 Elbow Connector to Aero-Coalescer
62 Aero-Coalescer Increasing Cross Section Portion
64 Aero-Coalescer Constant or Uniform Cross Section Portion
66 Aerodynamic Flow Separation Means
67 Aerodynamic Flow Separation Means (Different Shape)
68 First Aero-Coalescer Exit Duct
69 Fan (Optional) located at the Exit Duct of the Aero-Coalescer
70 First Aero-Coalescer Liquid Exit Line
72 Second Aerodynamic Gas Cleaning (ADGC) Reactor (or Sulfur Oxides ADGC Reactor)
74 Alkali Metal Hydroxide Carbonate-Bicarbonate Feed Line for Recycle Solution
76 Second Aero-Coalescer
78 Second Aero-Coalescer Liquid Removal Line
84 Second Aero-Coalescer Exit Duct
85 Third Aerodynamic Gas Cleaning (ADGC) Reactor (or First Nitrogen Oxides ADGC Reactor)
86 Alkali Metal Hydroxide-Carbonate-Bicarbonate Feed Line for Recycle Solution
88 Fourth Aerodynamic Gas Cleaning (ADGC) Reactor (or Second Nitrogen Oxides ADGC Reactor)

APPENDIX 1

90 Third Aero-Coalescer
92 Third Aero-Coalescer Liquid Removal Line
93 Solids Prefilter Unit
96 Third Aero-Coalescer Exit Duct
97 Induced Draft Fan located down-line after all of the Aero-Coalescers
98 Exit Discharge Stack
100 Exit Stack Gas Reheater
102 Exit Stack Gas Demister (Optional)
104 Exit Stack Gas Condenser (Optional)
106 Demister Water Supply Line (Optional)
108 Stack Gas Water Removal Line
109 Carbon Dioxide Condenser Liquid Line
110 Condensate Water Treatment Plant
111 Treated Water Removal Line
112 Ash Stream Acidic Extraction Unit
113 $CO_2$ and $H_2O$ Condenser Water and Stack Gas Water Line (Inlet Stream to Water Treatment Plant)
114 Ash Stream Alkaline Extraction Unit
115 Alkali Metal (Potash) Salt Feed Solution
116 Metals-Solids Recovery System
117 Ethanol Fermentation Unit
118 Reconstituted Alkali Metal Chloride Feed Stream
119 Ethanol Liquid Stream
120 Alkali Metal (Potassium) Chloride Electrolysis Cell
121 Ethylene Gas Stream 122 Alkali Metal (Potassium) Chloride Solution Mix Tank (an alternate tank/storage—optional)
123 Sulfur Oxides Chemical Recovery System
124 Sulfur Oxides Thermal Decarbonation Unit
125 Air Supply Line
126 Sulfur Oxides/Sulfite/Sulfate Oxidation Unit
127 Carbon Dioxide Gas Vent Line from Sulfurous Solution
128 Steam Heating Line

APPENDIX 1

130 Alkali Metal Sulfate Mix Tank
131 Alkali Metal Sulfate Precipitation Solution
132 Sulfate Evaporation Crystallization Unit
133 Mercuric Sulfate Precipitated Solids Stream
134 Alkali Metal (Potassium) Sulfates
136 Alkali Metal Carbonate Return Solution
137 Return Solution Bleed Stream
138 Alkali Metal Hydroxide Solution
139 Alkali Metal (Potassium) Carbonate Feed Stream
140 Recycled Liquid Mixing Tank from Sulfur Reactor System
141 Nitrogen Oxides Chemical Recovery System
142 Mixing Tank for Spent Liquid from Nitrogen Reactor System
143 Nitrogen Oxides Recovery Solution Feed Line
144 Nitrogen Oxides/Nitrite/Nitrate Oxidation Unit
145 Recirculating Product Liquid Media of Alkali Metal Nitrite/Nitrate Solution
146 Hydrogen Peroxide Solution, a Branch from Line 18
148 Nitrogen Oxides Thermal Decarbonation Unit
149 Alkali Metal Nitrate Decarbonation Recirculation Line
150 Water Vapor Exit Vent Line from the Sulfate Evaporator
151 Water Vapor Condenser
152 Carbon Dioxide Gas Vent Line from the Nitrate Decarbonation Unit
153 Water Vapor Exit Line from the Nitrate Evaporator
154 Carbon Dioxide Condenser
155 Carbon Dioxide Exit Gas Stream
156 Refrigeration Cooling Unit
157 Water Vapor Condenser Liquid Condensate Line
158 Nitrates Evaporation Crystallization Unit
159 Alkali Metal Sulfate Decarbonation Recirculation Line
160 Alkali Metal (Potassium) Nitrates
161 Return Alkali Metal Carbonate Solution from Nitrate System
162 Water Line
163 Process Heat Input
164 Alkali Metal Chloride Feed Solution
165 Effluent Wash Liquid
166 Hydrogen Gas Line
168 Chlorine Gas Line

APPENDIX 1

170 Ethylene Cracking Unit
171 Air Separation Plant
172 Hydrogen Peroxide Generation Unit
174 Hydrochloric Acid Production Unit
175 Hydrochloric Acid Liquid Stream
176 Ethylene Dichloride Production Unit
177 Ethylene Dichloride Product Stream
178 Vinyl Chloride Production Unit
179 Vinyl Chloride Monomer Product Stream
180 Polyvinyl Chloride Production Unit
181 Polyvinyl Chloride (PVC) Product
184 Chlorine Dioxide Production Unit
186 Selenium Removal System
188 Selenium Removal Prefilter Unit
190 Feed Water or Alkali Metal Chloride Solution
192 Filtered Spent Reagent Solution
193 Spent Liquid Feed Line to Metals Separation Process Unit 34
194 Spent Liquid from the Nitrogen Compounds Recirculating Wash Solution
195 Combined Metal Prefilter Recirculating Wash Solution with Metals Aero-Coalescer Liquid Effluent
196 Desulfurization Chemical Recovery Solution
198 Selenium Ion Exchange Demineralization Bed
199 Cleaned and Regenerated Ion Exchange Demineralization Resin
200 Liquid Bypass Stream
201 Additional Ion Exchange Demineralization Step
202 Selenium Recovery Step
203 Ion Exchange Regenerant Solution
204 Selenium Solution
205 Discharge Line from Selenium Ion Exchange Step 198 to Mixing Tank 140
206 Bottom Ash Stream
208 Fly Ash Stream
209 Alkali Metal (Potash) Solution Mix Tank
210 Unrecovered Fly Ash
212 Unrecovered Bottom Ash
213 Return Liquid Cleaning Unit
214 Unextracted Potash and Other Liquids
215 Return Liquid Wash Solids

APPENDIX 1

216 Ash Water Effluent Stream
217 Combined Water Wash Liquid
218 Waste Solids for Disposal
219 Ash Water Washing Unit
220 Water Washing Unit
222 Recovered Metals Acidic Extraction Unit
224 Recovered Metals Alkaline Extraction Unit
225 Recovered Metals Alkaline Extraction Liquid
228 Hydrochloric Acid Extraction Effluent
229 Nitric Acid Extraction Solution
230 Alkali Metal (Potassium) Hydroxide Extraction Effluent
231 Ash Stream Metals Recovery System
232 Combined Stream Metals Extraction System
233 Combined Alkaline Extraction Liquid (from #225 and #230)
234 Metals Oxidation Extraction Unit
235 Oxidation Extraction Liquid Stream
236 Nitrate Extraction Unit
237 Nitrate Extraction Exit Liquid
238 Metals Carbonate Extraction Unit
239 Carbonate Extraction Liquid Stream
240 Metals Organic Extraction Unit
241 Organic Extraction Exit Liquid
242 Recovered Metals Product, Exit Stream
243 Return Liquids Treatment Unit
244 Recovered Metals Storage Facility
245 Potassium Sulfate Drying Unit
246 Potassium Sulfate Bagging Unit
247 Potassium Nitrate Drying Unit
248 Potassium Nitrate Bagging Unit
249 Aluminum Oxide Recovery System
250 Aluminum Metals Recovery Unit
251 Recovered Aluminum Hydroxide Solids
252 Aluminum Hydroxide Drying Unit
253 Recovered Aluminum Oxide Stream 255 Nitrate Extraction Exit Solution
256 Uranium Oxide Recovery System
257 Uranium Hydroxide Precipitation Unit
258 Uranium Hydroxide Exit Solids
259 Uranium Recovery Exit Liquid to Carbonate Extraction Feed Line

APPENDIX 1

260 Uranium Hydroxide Drying Unit
261 Recovered Uranium Oxide Solids
262 Aluminum Oxide Dryer Vent Gas (to Water Vapor Condenser #151)
263 Uranium Oxide Dryer Vent Gas (to Water Vapor Condenser #151)
264 Combined Oxide Dryer Vent Gas (to Water Vapor Condenser #151)
266 Elongated Cylindrical Section
268 End Plate—Incoming End
270 End Plate—Outgoing End
271 Bolts
272 Reflective Surface
274 Quartz or Glass Body
276 Central Space
278 Annular Space
280 Air Pump
282 Air Lines
284 Air Nozzles
286 $H_2O_2$ Atomizer Nozzle
288 $Cl_2$ & $ClO_2$ Nozzle
290 Water Lines
292 Water Swirl Nozzles
294 Ultraviolet Lamps
296 Rings
297 Grommets
298 UV Lamps Power Supply
300 Electric Leads
302 Free Radical Line (Annular)
304 Free Radical Line (Central)
306 Combined Free Radical Line
308 Heater for Free Radicals
309 Heater for Air Duct
310 Sodium Hydroxide (Sulfur Oxides System)
311 Mixing Chamber for combining Free Radicals and Hot Air
312 Sodium Carbonates and Bicarbonates
314 Mixing Tank (Sulfur Oxides System)
316 Sodium Hydroxide (Nitrogen Oxides System)
318 Sodium Carbonates and Bicarbonates

APPENDIX 1

320 Mixing Tank (Nitrogen Oxides System)
322 Electrolysis Cell
324 Salt (NaCl)
326 Water
327 Electricity
328 Sodium Hydroxide
330 Hydrogen Gas
332 Chlorine Gas
334 Spent Scrubber Liquid
336 Mixing Tank
338 Salt Water Solution
340 Tank
342 Brackish Water
344 Brine Water
346 Oil Floatation Separation Unit
348 Solution
350 Algae Pond
352 Seed Organism
354 Phosphoric Acid
356 Sunlight or Artificial Light
358 Oxygen
360 Excess Water
362 Algae Solids
363 Algae Solids Recirculation Line
364 BioDiesel or Oil Refinery Unit
366 BioDiesel Oil
368 Shift Conversion Reactor
370 Carbon Monoxide
372 Methanol Synthesis
374 Methanol
376 Ethylene Cracking Unit
378 Ethylene
380 Ethanol Synthesis Reactor
382 Ethanol
384 Gasoline
386 Catalyst for Synthesizing Gasoline

APPENDIX 1

Number Identifiers For FIGS. 12a and 12b

400 Solid Waste
402 Auxiliary Fuel
404 Fourth Stage Aerodynamic Gas Cleaning (ADGC) Reactor
406 Fourth Stage Aero-Coalescer
407 Exit Duct from Aero-Coalescer 90A
408 Alkali Metal hydroxide Carbonate-Bicarbonate Solution
410 Mixing Tank
412 Mixing Tank
414 Mixing Tank
416 Withdrawal Line
418 Filter
420 Thermal Decarbonator
422 Oxidizer
424 Cooler
426 Evaporator-Crystallizer
428 Liquid Effluent
429 Bleed Stream
430 Saturated Carbon Dioxide Gas
432 Potassium (Alkali Metal) Sulfate
434 Potassium (Alkali Metal) Nitrate
436 Return Line
438 Line
440 Filter
442 Thermal Decarbonator
446 Effluent Liquid Stream
448 Bleed Stream
450 Filter
452 Withdrawal Line
454 Oxidizer
456 Thermal Decarbonator
458 Cooler
460 Evaporator-Crystallizer
462 Condenser
464 Line
466 Bleed Stream
468 Filter
470 Acidulation Reactor

APPENDIX 2

Listing of Process Chemical Reactions

Hydrogen Peroxide Chemical Reactions
Hydrogen Peroxide Formation $H_2O_2 + UV\ Light \dashrightarrow 2\ OH^*$ $H_2O_2 + OH^* \dashrightarrow HO_2^* + H_2O$ Nitrogen Oxides Reactions $NO + OH^* \dashrightarrow HNO_2$ $NO_2 + OH^* \dashrightarrow HNO_3$ $NO + HO_2^* \dashrightarrow HNO_3$ $NO + HO_2^* \dashrightarrow NO_2 + OH^*$ $2\ NO + O_2 \dashrightarrow 2\ NO_2$ Elemental Mercury Reactions $Hg + 2\ OH^* \dashrightarrow HgO + H_2O$ $Hg + HO_2^* \dashrightarrow HgO + OH^*$ $Hg + 2\ Cl^* \dashrightarrow HgCl_2$ $Hg + 2\ OCl^* \dashrightarrow Hg(OCl)_2$ Hydrogen Peroxide Reactions $2\ NO_2 + H_2O \dashrightarrow HNO_2 + HNO_3$ $2\ NO_2 + H_2O_2 \dashrightarrow 2\ HNO_3$ $HNO_2 + H_2O_2 \dashrightarrow HNO_3 + H_2O$ $K_2SO_3 + H_2O_2 \dashrightarrow K_2SO_4 + H_2O$

APPENDIX 2

Chlorine Compound Chemical Reactions
Chlorine Gas Reactions $Cl_2 + UV\ Light \dashrightarrow 2\ Cl^*$ $Cl_2 + H_2O \dashrightarrow HOCl + HCl$ $Cl_2 + NO + H_2O \dashrightarrow 2\ HCl + NO_2$ Mercury Compound Reactions $Hg + Cl_2 \dashrightarrow HgCl_2$ $HgO + H_2O \dashrightarrow Hg(OH)_2$ $Hg(OH)_2 + 2\ HCl \dashrightarrow HgCl_2 + 2\ H_2O$ $Hg(OH)_2 + 2\ HOCl \dashrightarrow Hg(OCl)_2 + 2\ H_2O$ $Hg(OCl)_2 + H_2O \dashrightarrow HgCl_2 + H_2O_2$ Chlorine Dioxide Reactions $ClO_2 + UV\ Light \dashrightarrow 2\ ClO^* + O^*$ $O_2 + Cl_2 + 2\ H_2O_2 \dashrightarrow 2\ ClO_2 + 2\ H_2O$ $NO_2 + ClO_2 + H_2O \dashrightarrow HNO_3 + HCl$ $NO_2 + ClO_2 + H_2O \dashrightarrow HNO_3 + HCl + O_2$ $Hg(OH)_2 + 2\ HOCl \dashrightarrow Hg(OCl)_2 + 2\ H_2O$

Carbon and Organic Reactions
Carbon Monoxide Reactions $2\ CO + O_2 \dashrightarrow 2\ CO_2$ $CO + 2\ OH^* \dashrightarrow CO_2 + H_2O$ $CO + HO_2^* \dashrightarrow C_2 + OH^*$ $CO + 2\ HO_2^* \dashrightarrow CO_2 + 2\ OH^* + O^*$ $2\ CO + O_2 \dashrightarrow 2\ CO_2$ $CO + O^* \dashrightarrow CO_2$ Organic Compound Reactions $[CH] + O_2 \dashrightarrow CO_2 + H_2O$ $[CH] + OH^* \dashrightarrow CO_2 + H_2O$ $[CH] + HO_2^* \dashrightarrow CO + OH^*$

Flue Gas Stream Chemical Reactions
Sulfur Oxides Reactions $SO_2 + H_2O \dashrightarrow H_2SO_3$ $H_2SO_3 ==== H^+ + HSO_3^- ==== 2\ H^+ + SO_3^{-2}$ $2\ H_2SO_3 + O_2 \dashrightarrow 2\ H_2SO_4$ $H_2SO_3 + 2\ KOH \dashrightarrow K_2SO_3 + 2\ H_2O$ $H_2SO_4 + 2\ KOH \dashrightarrow K_2SO_4 + 2\ H_2O$ Nitrogen Oxides Reactions $2\ NO_2 + H_2O \dashrightarrow HNO_2 + HNO_3$ $2\ NO_2 + H_2O_2 \dashrightarrow 2\ HNO_3$

APPENDIX 2

$HNO_2 + H_2O_2 \dashrightarrow HNO_3 + H_2O$ $HNO_2 === H^+ + NO_2^- === HNO_2 + KOH ==== KNO_2 + H_2O$ Carbon Dioxide Reactions $CO_2 + H_2O \dashrightarrow H_2CO_3$ $H_2CO_3 ==== H^+ + HCO_3^- ==== 2\ H^+ + CO_3^{-2}$ $H_2CO_3 + 2\ KOH \dashrightarrow K_2CO_3 + H_2O$ $H_2CO_3 + KOH \dashrightarrow KHCO3 + H_2O$ Sulfur Oxides Removal Reactions $H_2O + SO_2 \dashrightarrow H_2SO_3$ $H_2O + SO_3 \dashrightarrow H_2SO_4$ $H_2SO_3 + 2\ KOH \dashrightarrow K_2SO_3 + H_2O$ $H_2SO_3 + KOH \dashrightarrow KHSO_3 + H_2O$ $H_2SO_3 + 2\ K_2CO_3 \dashrightarrow K_2SO_3 + H_2CO_3$ $2\ K_2SO_3 + O_2 \dashrightarrow 2\ K_2SO_4$ $SO_2 + 2\ KHCO_3 \dashrightarrow K_2SO_3 + 2\ CO_2 + H_2O$ $SO_2 + 2\ KHCO_3 + H_2O_2 \dashrightarrow K_2SO_4 + 2\ CO_2 + 2\ H_2O$ $K_2SO_3 + H_2O_2 \dashrightarrow K_2SO_4 + H_2O$ $SO_2 + K_2CO_3 \dashrightarrow K_2SO_3 + CO_2$ $2\ KHCO_3 + Heat \dashrightarrow K_2CO_3 + CO_2 + H_2O$ $KHSO_3 + Heat \dashrightarrow$ Negligible Reaction Occurs $KHSO_3 + KHCO_3 \dashrightarrow K_2SO_3 + CO_2 + H_2O$

APPENDIX 2

$2\ K_2SO_3 + O_2 \dashrightarrow 2\ K_2SO_4$ $K_2CO_3 + O_2 \dashrightarrow$ Negligible Reaction Occurs

Nitrogen Oxides Removal Reactions $H_2O + 2\ NO_2 \dashrightarrow HNO_2 + HNO_3$ $HNO_2 + KOH \dashrightarrow KNO_2 + H_2O$ $HNO_3 + KOH \dashrightarrow KNO_3 + H_2O$ $2\ KNO_2 + O_2 \dashrightarrow 2\ KNO_3$ $KNO_2 + H_2O_2 \dashrightarrow KNO_3 + H_2O$ $2\ NO + H_2O_2 + 2\ K_2CO_3 \dashrightarrow 2\ KNO_3 + 2\ KHCO_3$ $NO + H_2O_2 + K_2CO_3 \dashrightarrow KNO_2 + KNO_3 + H_2O$ $2\ KHCO_3 + Heat \dashrightarrow K_2CO_3 + CO_2 + H_2O$ $KHSO_3 + KHCO_3 \dashrightarrow K_2SO_3 + CO_2 + H_2O$ $KNO_2 + H_2O_2 \dashrightarrow KNO_3 + H_2O$ $2\ HNO_2 + K_2CO_3 \dashrightarrow 2\ KNO_2 + H_2O + CO_2$ $2\ HNO_3 + K_2CO_3 \dashrightarrow 2\ KNO_3 + H_2O + CO_2$

Metal Removal and Recovery Reactions
Metal Washing Treatment Reactions

Metals+Inorganics+Water $\dashrightarrow$ Metal Extract+Insoluble Ash

Metals+Inorganics+HCl $\dashrightarrow$ Metal Chlorides+Insoluble Ash

Metals+Inorganics+KOH $\dashrightarrow$ Metal Hydroxide+Insoluble Ash

APPENDIX 2

Metal Extraction Chemical Reactions
Metals+Inorganics+$H_2O_2$ $\dashrightarrow$ Oxidized Metals+Insoluble Ash Metals+Inorganics+$K_2CO_3$ $\dashrightarrow$ Metal Carbonate+Insoluble Ash Metals+Inorganics+$C_2H_5OH$ $\dashrightarrow$ Metallic Organics+Insoluble Ash Metals+Inorganics+KCl $\dashrightarrow$ Metal Chlorides+Insoluble Ash

Aluminum Recovery Reactions $Al_2O_3$ (Solid)+3 $H_2O$ (Liquid) $\dashrightarrow$ 2 $Al(OH)_3$ (Precipitate in Solution)

2 $Al(OH)_3$ (Base)+6 HCl (Acid) $\dashrightarrow$ 2 $AlCl_3$ (Salt)+3 $H_2O$ (Liquid)

$AlCl_3$ (Salt)+3 KOH (Base) $\dashrightarrow$ $Al(OH)_3$ (Base)+3 KCl (Salt)

2 $Al(OH)_3$+Heat $\dashrightarrow$ $Al_2O_3$ (Solid)+3 $H_2O$ (Vapor)

Uranium Extraction Unit $U_3O_8 + H_2O_2 \dashrightarrow 3\ UO_3 + H_2O$ $UO_3 + 6\ HNO_3 \dashrightarrow U(NO_3)_6 + 3\ H_2O$ $U(NO_3)_6 + 6\ KOH \dashrightarrow U(OH)_6 + 6\ HNO_3$ $U(OH)_6 + Heat \dashrightarrow UO_3 + 3\ H_2O$

Fertilizer Drying Operations
Potassium Sulfate $K_2SO_4 \cdot xH_2O$ (Solid)+Heat $\dashrightarrow K_2SO_4$ (Crystals)+$H_2O$ (Vapor)

Potassium Nitrate $KNO_3 \cdot xH_2O$ (Solid)+Heat $\dashrightarrow KNO_3$ (Crystals)+$H_2O$ (Vapor)

APPENDIX 2

Algae Photosynthesis and BioDiesel Oil Production

Salt Electrolysis $$2\ NaCl + 2\ H_2O \xrightarrow{Electrolysis} 2NaOH + H_2 + Cl_2$$

Caustic Soda Carbonation $NaOH + H_2CO_3 \dashrightarrow NaHCO_3 + H_2O$ $2\ NaOH + H_2CO_3 \dashrightarrow Na_2CO_3 + 2\ H_2O$ Carbonic Acid Dissociation $H_2O + CO_2 \rightleftharpoons H_2CO_3 \rightleftharpoons H^+ + HCO_3^- \rightleftharpoons 2H^+ + CO_3^{-2}$ Algae Photosynthesis $$CO_2 + H_2O + NaNO_3 + H_3PO_4 + Na_2SO_4 \xrightarrow{Sunlight} [CHONPKS]_{Algae\ Cells} + O_2$$

BioDiesel Oil Refining $$[CHONPKS]_{Algae\ Cells} + H_2O + H_2 \xrightarrow{Heat} [CHONPKS]_{BioDiesel\ Oil} + Solids + H_2O$$

Transportation Fuels Production

Carbon Monoxide Shift Reactions $$CO_2 + C \xrightarrow{Heat} 2\ CO$$
$$CO + H_2O \longrightarrow CO_2 + H_2$$
$$CO_2 + H_2 \longrightarrow CO + H_2O$$

APPENDIX 2

Methanol Production Reactions (Methanol)
$$CO + 2H_2 \xrightarrow[\text{Catalyst + Heat}]{\text{CrO, ZnO}} CH_3OH$$

(Ethylene)
$$2CH_3OH \xrightarrow{\text{Heat}} C_2H_4 + 2H_2O$$

Ethanol Production Reactions (Ethanol)
$$2CO + 4H_2 \xrightarrow[\text{Catalyst + Heat}]{\text{CrO, ZnO}} C_2H_5OH + H_2O$$

(Ethanol)
$$C_2H_4 + H_2O \longrightarrow C_2H_5OH$$

Hydrogen Generation Reactions $$2H_2O \xrightarrow{\text{Electrolysis}} 2H_2 + O_2$$
$$CH_4 + 2H_2O \xrightarrow{\text{Heat + Steam}} CO_2 + 4H_2$$

What is claimed is:

1. A process for capturing and removing carbon dioxide gas, heavy metals, particulates, oxides of sulfur, oxides of nitrogen, or a mixture thereof, from a combustion gas mixture stream comprising:

a) driving said combustion gas mixture stream through a first aerodynamic reactor with a first free jet formed from a first compressible fluid, said first free jet having incorporated therein first atomized liquid droplets or vapor;

b) encapsulating said metals or said particulates into first liquid droplets and growing said first liquid droplets into first larger droplets by diffusion, condensation, impaction, interception, or a combination thereof;

c) separating said first larger droplets from said combustion gas mixture stream in a first gas/liquid separator to form a first effluent gas mixture and a first effluent liquid stream;

d) driving said first effluent gas mixture through a second aerodynamic reactor with a second free jet formed from a second compressible fluid, said second free jet having incorporated therein second atomized liquid droplets or vapor of an alkali metal alkaline solution;

e) reacting said second atomized liquid droplets or vapor of said alkali metal alkaline solution, said oxides of sulfur, or said oxides of nitrogen, and at least a portion of said carbon dioxide to form first reaction products in the form of second droplets;

f) growing said second droplets into second larger droplets by diffusion, condensation, impaction, interception, or a combination thereof;

g) separating said second larger droplets from said first effluent gas mixture in a second gas/liquid separator to form a second effluent gas mixture and a second effluent liquid stream;

h) treating said second effluent liquid stream through decarbonation, oxidation, evaporation, crystallization, or a combination thereof, whereby a portion of carbon dioxide gas and water vapor is liberated and alkali metal sulfate and nitrate is separated as a solid;

i) discharging said second effluent gas mixture.

2. A process for capturing and removing carbon dioxide gas, heavy metals, particulates, oxides of sulfur, oxides of nitrogen, or a mixture thereof, from a combustion gas mixture stream comprising:

a) driving said combustion gas mixture stream through a first aerodynamic reactor with a first free jet formed from a first compressible fluid, said first free jet having incorporated therein first atomized liquid droplets or vapor;

b) encapsulating said metals or said particulates into first liquid droplets and growing said first liquid droplets into first larger droplets by diffusion, condensation, impaction, interception, or a combination thereof;

c) separating said first larger droplets from said combustion gas mixture stream in a first gas/liquid separator to form a first effluent gas mixture and a first effluent liquid stream;

d) driving said first effluent gas mixture through a second aerodynamic reactor with a second free jet formed from a second compressible fluid, said second free jet having incorporated therein second atomized liquid droplets or vapor of an alkali metal alkaline solution;

e) reacting said second atomized liquid droplets or vapor of said alkali metal alkaline solution, said oxides of sulfur, and at least a portion of said carbon dioxide to form first reaction products in the form of second droplets;

f) growing said second droplets into second larger droplets by diffusion, condensation, impaction, interception, or a combination thereof;

g) separating said second larger droplets from said first effluent gas mixture in a second gas/liquid separator to form a second effluent gas mixture and a second effluent liquid stream;

h) treating said second effluent liquid stream through decarbonation, oxidation, evaporation, crystallization, or a combination thereof, whereby a first portion of carbon dioxide gas and water vapor is liberated and alkali metal sulfate is separated as a solid;

i) driving said second effluent gas mixture through a third aerodynamic reactor with a third free jet formed from a third compressible fluid, said third free jet having incorporated therein third atomized liquid droplets or vapor of an alkali metal alkaline solution;

j) reacting said third atomized liquid droplets or vapor of said alkali metal alkaline solution, said oxides of nitrogen, and at least a portion of said carbon dioxide to form second reaction products in the form of third droplets;

k) growing said third droplets into third larger droplets by diffusion, condensation, impaction, interception, or a combination thereof;

l) separating said third larger droplets from said second effluent gas mixture in a third gas/liquid separator to form a third effluent gas mixture and a third effluent liquid stream;

m) treating said third liquid effluent stream through oxidation, decarbonation, cooling, evaporation, crystallization, or a combination thereof, whereby a second portion of carbon dioxide gas and water vapor is liberated and alkali metal nitrate is separated as a solid;

n) discharging said third effluent gas mixture.

3. A process for capturing and removing carbon dioxide gas, heavy and trace metals, fly ash, large and small particulates, oxides of nitrogen and sulfur, carbon monoxide, organic compounds, or a mixture thereof, from a hot combustion gas mixture stream, comprising:

a) pressurizing said hot combustion gas mixture stream to give a pressurized hot combustion gas mixture stream;

b) conditioning said pressurized hot combustion gas mixture stream to remove large particulates and large fly ash particles and to reduce to temperature thereof to the range of about 250 to about 400° F. to give a conditioned combustion gas mixture stream;

c) treating said conditioned combustion gas mixture stream in a first aerodynamic reactor in which said conditioned combustion gas mixture stream is driven through a subsonic nozzle in part by a free jet exiting from at least one supersonic nozzle fed with a compressible fluid so as to form a supersonic free jet which, in conjunction with said subsonic nozzle, acts as an ejector pump, said supersonic free jet having incorporated therein atomized liquid droplets or vapor issuing from nozzles associated with said supersonic free jet and contacting said conditioned combustion gas mixture stream to form a turbulent subsonic free jet by passing through said subsonic nozzle into a downstream reaction chamber whereby the heavy and trace metals and the particulates provide nucleation sites for the encapsulation of said heavy and trace metals, and said particulates into liquid droplets under conditions of impaction, interception, condensation, diffusion, or a combination thereof, to be followed by droplet growth by means of impaction, interception, nucleation, condensation, or a combination thereof, into first larger liquid droplets;

d) removing said first larger liquid droplets from said conditioned combustion gas mixture stream in a first gas/liquid separator as a first liquid effluent stream containing said heavy and trace metals and said particulates;

e) removing said first liquid effluent stream for subsequent disposal or physical and chemical recovery;

f) discharging a first effluent gas stream comprising oxides of carbon, nitrogen and sulfur from said first gas/liquid separator;

g) treating said first effluent gas stream from said first gas/liquid separator in a second aerodynamic reactor for the removal of sulfur dioxide and a portion of the carbon dioxide, said aerodynamic reactor comprising a subsonic nozzle through which said first effluent gas stream is driven in part by a supersonic free jet exiting from at least one supersonic nozzle fed with a compressible fluid so as to form a supersonic free jet which, in conjunction with said subsonic nozzle, acts as an ejector pump, said supersonic free jet having incorporated therein atomized liquid droplets or vapor of an alkali metal alkaline solution issuing from nozzles associated with said supersonic free jet and contacting said first effluent gas stream to form a turbulent subsonic free jet by passing through said subsonic nozzle into a downstream reaction chamber, whereby said sulfur dioxide, said carbon dioxide, and said alkali metal alkaline solution are brought into intimate contact and react to produce reaction products in the form of second liquid droplets, said second liquid droplets growing by diffusion, impaction, interception, condensation, or a combination thereof, into second larger liquid droplets;

h) removing said second larger liquid droplets from said first effluent gas stream in a second gas/liquid separator as a second liquid effluent stream containing said liquid reaction products;

i) treating said second liquid effluent stream by filtration, washing by water or a metal chloride solution, said wash solution ducted for subsequent disposal or physical and chemical recovery;

j) passing said treated second liquid effluent stream to a first mixing tank;

k) treating a first portion of said second treated effluent stream from said first mixing tank through steps comprising decarbonation, oxidation, evaporation, crystallization, or a combination thereof, whereby a portion of carbon dioxide gas and water vapor is liberated and alkali metal sulfate is separated as a solid with recycle of the effluent liquid stream from said sequential decarbonation, oxidation, evaporation, crystallization, or a combination thereof, treatment to said first mixing tank;

l) adding water and an alkali metal alkaline solution to said first mixing tank;

m) circulating of a second portion of said second treated liquid effluent stream from said first mixing tank to said second aerodynamic reactor;

n) condensing said water vapor from said carbon dioxide and water vapor to produce carbon dioxide gas;

o) discharging the remainder of said first effluent gas stream as a second effluent gas stream comprising oxides of nitrogen and carbon dioxide from said second gas/liquid separator;

p) treating said second effluent gas stream from said second gas/liquid separator in a third aerodynamic reactor for the removal of said nitrogen oxides and an additional portion of said carbon dioxide, said third aerodynamic reactor comprising a subsonic nozzle through which said second effluent gas stream is driven in part by a supersonic nozzle fed with a compressible fluid so as to form a supersonic free jet which, in conjunction with said subsonic nozzle, acts as an ejector pump, said supersonic free jet having incorporated therein atomized liquid droplets or vapor of an alkali metal alkaline solution issuing from liquid nozzles associated with said supersonic free jet and contacting said second effluent gas stream to form a turbulent subsonic free jet by passing through said subsonic nozzle into a downstream reaction chamber, whereby said nitrogen oxides, said carbon dioxide, and said alkali metal alkaline solution, are brought into intimate contact and react to produce reaction products in the form of third liquid droplets growing by diffusion, impaction, interception, condensation, or a combination thereof, into third larger droplets;

q) removing said third larger droplets from said second effluent gas stream in a third gas/liquid separator as a third liquid effluent stream containing the said liquid reaction products;

r) treating said third liquid effluent stream by filtration washed by water or metal chloride solution with the effluent wash liquid removed for subsequent disposal or physical and chemical recovery;

s) passing said filtered liquid reaction products from said third effluent stream to a second mixing tank;

t) circulating a first portion of said filtered liquid effluent from said third effluent stream to said third aerodynamic reactor;

u) treating a second portion of said filtered liquid reaction products from said third effluent stream from said second mixing tank through oxidation, decarbonation, cooling, evaporation, crystallization, or a combination thereof, whereby carbon dioxide gas and water vapor are liberated and alkali metal nitrate is separated as a solid with recycle of the remaining product liquid stream to said second mixing tank;

v) adding water and alkali metal alkaline solution to said second mixing tank;

w) condensing said water vapor from said carbon dioxide gas and water vapor to produce carbon dioxide gas; and x) discharging the remainder of said second effluent gas stream as a third effluent gas stream.

4. A process according to claim 2, where the liquid droplets or vapor in step (a) comprise an alkali metal chloride solution.

5. A process according to claim 2, wherein the alkali metal alkaline solution in step (d) comprises a solution of potassium hydroxide and potassium carbonate-bicarbonate, and the alkali metal sulfate in step (h) comprises potassium sulfate.

6. A process according to claim 2, wherein the alkali metal alkaline solution in step (i) comprises a solution of potassium hydroxide and potassium carbonate-bicarbonate, and the alkali metal nitrate in step (m) comprises potassium nitrate.

7. A process according to claim 2, wherein the compressible fluid in steps (a), (d) and (i) comprises steam, air or gas.

8. A process according to claim 2, further comprising treating said combustion gas mixture stream prior to said first aerodynamic reactor with a stream of free radicals produced by photolysis of hydrogen peroxide, chlorine gas, chlorine dioxide gas, water, or a combination thereof and introducing a second stream of said first free radicals via said first atomized liquid droplets or vapor in step (a) for oxidizing mercury to mercury salts and other trace metals to their respective salts.

9. A process according to claim 8, wherein a third stream of said free radicals is introduced via said second atomized liquid droplets or vapor in step (d) for the oxidation of carbon monoxide gas and organic vapors to carbon dioxide gas and water vapor.

10. A process according to claim 9, wherein a fourth stream of said free radicals is introduced via said third atomized liquid droplets or vapor in step (i) for the oxidation of nitric oxide gas to nitrogen dioxide gas, carbon monoxide gas to carbon dioxide gas, and trace organic vapors to carbon dioxide gas and water vapor.

11. The process according to claim 2, wherein said first effluent liquid stream is further subjected to the following steps to separate mercury-containing pollutants, comprising:

a) removing insoluble particles from said effluent liquid stream giving a filtrate containing soluble mercury-containing pollutants;

b) passing said filtrate through an activated carbon adsorption bed to give a carbon-treated filtrate;

c) precipitating mercury salts from said carbon-treated filtrate with an alkaline solution capable of forming an insoluble salt with mercury.

12. The process according to claim 11 further comprising extracting said insoluble particles with an acidic solution to give soluble mercury salts.

13. The process according to claim 12 further comprising treating said soluble mercury salts with an alkaline solution capable of forming an insoluble salt with mercury.

14. The process according to claim 11 further comprising extracting said insoluble particles with an alkaline solution to give oxides or hydroxides of a first group of metals.

15. The process according to claim 11 further comprising extracting said insoluble particles with an oxidative solution to give oxidized products of a second group of metals.

16. The process according to claim 11 further comprising extracting said insoluble particles with nitric acid to give soluble uranium compounds followed by treating said soluble uranium compounds with an alkaline solution to give solid uranium compounds.

17. The process according to claim 11 further comprising extracting said insoluble particles with carbonate to give metal carbonates.

18. The process according to claim 11 further comprising extracting said insoluble particles with an organic solvent to give metal organic complexes.

19. The process according to claim 2 further comprising the steps of: passing said treated second effluent liquid stream from step h) through a first ion exchange demineralization resin bed to remove selenium ions.

20. A process for the production of BioDiesel fuel in accordance with claim 2, wherein the alkali metal alkaline solution in steps (d) and (i) comprises a solution of sodium hydroxide and sodium carbonate-bicarbonate, the alkali metal sulfate in step (h) comprises sodium sulfate, and the alkali metal nitrate in step (m) comprises sodium nitrate, and further comprising, the steps of:

a) combining a portion of said second and third effluent streams into a mixing tank;

b) introducing a brine solution into said mixing tank;

c) feeding the solution from said mixing tank into an algae pond;

d) introducing seed organisms into said algae pond;

e) treating said algae pond with sunlight or artificial light to promote the growth of algae solids;

f) harvesting said algae solids from said algae pond;

g) fermenting said algae solids to produce BioDiesel fuel.

21. A process for the production of ethanol fuel in accordance with claim 2, wherein the alkali metal alkaline solution in steps (d) and (i) comprises a solution of sodium hydroxide and sodium carbonate-bicarbonate, the alkali metal sulfate in step (h) comprises sodium sulfate, and the alkali metal nitrate in step (m) comprises sodium nitrate, and further comprising the steps of:

a) combining a portion of said second and third effluent streams into a mixing tank;

b) introducing a brine solution into said mixing tank;

c) feeding the solution from said mixing tank into an algae pond;

d) introducing seed organisms into said algae pond;

e) treating said algae pond with sunlight or artificial light to promote the growth of algae solids;

f) harvesting said algae solids from said algae pond;

g) fermenting said algae solids to produce ethanol fuel.

22. A process for the production of methanol from carbon dioxide gas in accordance with claim 2 and further comprising the steps of:

a) reacting said carbon dioxide gas liberated in steps (h) and (m) with hydrogen gas and steam in a shift reactor to produce carbon monoxide gas and water vapor;

b) reacting said carbon monoxide gas with additional hydrogen in a methanol synthesis reactor to produce methanol.

23. A process for the production of ethylene gas from carbon dioxide in accordance with claim 22 and further comprising the step of reacting said methanol with heat and hydrogen gas in an ethylene cracking unit to form ethylene gas.

24. A process for the production of ethanol from carbon dioxide in accordance with claim 23 and further comprising the step of reacting said ethylene gas with water and hydrogen in an ethanol synthesis reactor to produce ethanol.

25. A process for the production of ethylene dichloride from carbon dioxide gas according to claim 23 and further comprising the step of reacting said ethylene gas with chlorine gas in a reactor to produce ethylene dichloride.

26. A process for the production of gasoline in accordance with claim 22 and further comprising the step of reacting said methanol in a gasoline synthesis reactor to produce gasoline.

27. A process for the production of vinyl chloride from carbon dioxide gas in accordance with claim 25 and further comprising the step of reacting said ethylene dichloride with ethylene gas to produce vinyl chloride.

28. A process for the production of polyvinyl chloride from carbon dioxide gas in accordance with claim 27 and further comprising the step of reacting said vinyl chloride with additional ethylene gas to produce polyvinyl chloride.

29. An apparatus for removing particulate contaminants and gaseous substances from a polluted gas stream and for recovering desirable by-products from said polluted gas stream, said apparatus comprising:
   a) a first aerodynamic reactor having:
      (i) a first inlet section having a first outlet mouth;
      (ii) a first reactor chamber having a first inlet end and a first outlet end, said first reactor chamber first inlet end connected to said first outlet mouth of said first inlet section;
      (iii) a first nozzle connected to said first outlet mouth of said first inlet section, said first nozzle having a first throat and at least one first aperture in said first throat;
      (iv) at least one second nozzle located within said first inlet section creating a first free jet of a compressible fluid to drive and create a turbulent mixture of said polluted gas stream and driving said first free jet through said first nozzle to form a second free jet in said first reactor chamber;
      (v) at least one first liquid atomizing or vapor nozzle associated with at least one of said at least one second nozzle and said first nozzle of said first aerodynamic reactor;
   b) a first gas/liquid separator connected to said first outlet end of said first reactor chamber to separate said particulate contaminants from said polluted gas stream to provide first separated gaseous substances;
   c) a second aerodynamic reactor communicating with said first separated gaseous substances, said second aerodynamic reactor having:
      (i) a second inlet section having a second outlet mouth;
      (ii) a second reactor chamber having a second inlet end and a second outlet end, said second reactor chamber second inlet end connected to said second outlet mouth of said second inlet section;
      (iii) a third nozzle connected to said second outlet mouth of said second inlet section, said third nozzle having a third throat and at least one third aperture in said third throat;
      (iv) at least one fourth nozzle located within said second inlet section creating a third free jet of compressible fluid to drive and create a turbulent mixture of said first separated gaseous substances and driving said third free jet through said third nozzle to form a fourth free jet in said second reactor chamber;
      (v) at least one second liquid atomizing or vapor nozzle associated with at least one of said at least one fourth nozzle and said third nozzle of said second aerodynamic reactor; and
   d) a second gas/liquid separator connected to said second outlet end of said second reactor chamber to separate liquid by-products from said first separated gaseous substances to provide second separated gaseous substances.

30. The apparatus of claim 29, wherein said at least one second nozzle comprises a supersonic nozzle.

31. The apparatus of claim 29, wherein said first free jet of compressible fluid comprises steam, air, or a gas.

32. The apparatus of claim 29, wherein said first reactor chamber of said first aerodynamic reactor contains a first enlarged cross-section portion at the inlet end thereof 33. The apparatus of claim 29, wherein said at least one fourth nozzle comprises a supersonic nozzle.

34. The apparatus of claim 29, wherein said third free jet of compressible fluid comprises steam, air, or a gas.

35. The apparatus of claim 29, wherein said second reactor chamber of said second aerodynamic reactor contains a second enlarged cross-section portion at the inlet end thereof 36. The apparatus of claim 29, further comprising at least a third aerodynamic reactor and a third gas/liquid separator connected in series.

* * * * *